United States Patent
Donovan et al.

(10) Patent No.: US 9,068,204 B2
(45) Date of Patent: Jun. 30, 2015

(54) PEPTIDOGLYCAN HYDROLASE ANTIMICROBIALS FOR ERADICATING LACTOBACILLI THAT CONTAMINATE AND REDUCE ETHANOL YIELDS IN BIOFUEL FERMENTATION

(71) Applicant: The United States of America, as represented by the Secretary of Agriculture, Washington, DC (US)

(72) Inventors: David M. Donovan, Baltimore, MD (US); Dwayne R. Roach, Laurel, MD (US); Piyum A. Khatibi, Dunlap, IL (US); Kenneth M. Bischoff, Morton, IL (US); Stephen R. Hughes, Peoria, IL (US)

(73) Assignee: The United States of America, as Represented by the Secretary of Agriculture, Washington, DC (US)

( * ) Notice: Subject to any disclaimer, the term of this patent is extended or adjusted under 35 U.S.C. 154(b) by 140 days.

(21) Appl. No.: 13/837,654

(22) Filed: Mar. 15, 2013

(65) Prior Publication Data
US 2014/0273137 A1 Sep. 18, 2014

(51) Int. Cl.
| | |
|---|---|
| C12P 7/10 | (2006.01) |
| C12P 7/06 | (2006.01) |
| C12N 9/00 | (2006.01) |
| C12N 1/20 | (2006.01) |
| C12N 15/00 | (2006.01) |
| C12N 9/36 | (2006.01) |

(52) U.S. Cl.
CPC ...... *C12P 7/10* (2013.01); *C12P 7/06* (2013.01); *Y02E 50/16* (2013.01); *Y02E 50/17* (2013.01); *C12N 9/2462* (2013.01)

(58) Field of Classification Search
None
See application file for complete search history.

(56) References Cited

U.S. PATENT DOCUMENTS

| | | |
|---|---|---|
| 2011/0243915 A1 | 10/2011 | Briers et al. |
| 2012/0189606 A1 | 7/2012 | Lavigne et al. |

OTHER PUBLICATIONS

Beckner, M. et al., Microbial Contamination of Fuel Ethanol Fermentations, Letters in Applied Microbiology, 2011, 387-394, vol. 53.
Bischoff, K.M. et al., Antimicrobial Susceptibility if *Lactobacillus* Species Isolated from Commercial Ethanol Plants, J Ind Microbiol Biotechnol, 2007, 739-744, vol. 34.
Bischoff, K.M. et al., Modeling Bacterial Contamination of Fuel Ethanol Fermentation, Biotechnology and Bioengineering, 2009, 117-122, vol. 103 (1).
Limayem, A. et al., Alternative Antimicrobial Compounds to Contrl Potential *Lactobacillus* Contamination in Bioethanol Fermentations, Journal of Environmental Science and Health, Part B, 2011, 709-714, vol. 46.
Loeffler, J.M. et al., Rapid Killing of *Streptococcus pneumoniae* with a Bacteriphage Cell Wall Hydrolase, www.sciencemag.org, Science, 2001, 2170-2172, vol. 294.
Makanjuola, D.B. et al., Some Effects of Lactic Acid Bacteria on Laboratory-Scale Yeast Fermentations, Enzyme Microb. Technol., 1992, 350-357, vol. 14.
Narendranath, N.V. et al., Effects of Lactobacilli on Yeast-Catalyzed Ethanol Fermentations, Appl. Environ, Microbiol., 1997, 4158-4163, vol. 63 (11).
Nelson, D. et al., Prevention and Elimination of Upper Respiratory Colonization of Mice by Group A. Streptococci by Using a Bacteriophage Lytic Enzyme, PNAS, 2001, 4107-4112. vol. 98 (7).
Schell, D.J. et al., Contaminant Occurrence, Identification and Control in a Pilot-Scale Corn Fiber to Ethanol Conversion Process, Bioresource Technology, 2007, 2942-2948, vol. 98.
Schmelcher, M. et al., Chimeric Phage Lysins Act Synergistically with Lysostaphin to Kill Mastitis-Causing *Staphylococcus aureus* in Murine Mammary Glands, Applied and Environmental Microbiology, 2012, 2297-2305, vol. 78 (7).
Schnurer, J. et al., Antifungal Lactic Acid Bacteria as Biopreservatives, Trends in Food Science and Technology, 2005, 70-78, vol. 16.
Schuch, F. et al., A Bacteriolytic Agent that Detects and Kills *Bacillus antracis*, Nature, 2002, 884-889, vol. 418.
Skinner, K.A. et al., Bacterial Contaminants of Fuel Ethanol Production. J Ind. Microbiol Biotechnol, 2004, 401-40-8. vol. 31.

*Primary Examiner* — Christian Fronda
(74) *Attorney, Agent, or Firm* — John D. Fado; Evelyn M. Rabin

(57) ABSTRACT

Ethanol losses due to bacterial contamination in fermentation cultures weakens the economics of biofuel production. *Lactobacillus* species are the predominant contaminant. Bacteriophage lytic enzymes are peptidoglycan hydrolases which degrade Gram positive cell walls when exposed externally and are a novel source of antimicrobials. The streptococcal phage λSA2 endolysin construct demonstrated strong lytic activity towards 17 of 22 strains of lactobacilli, staphylococci or streptococci maintaining optimal specific activity under fermentation conditions toward *L. fermentum* substrates. *Lactobacillus* bacteriophage endolysin constructs LysA, LysA2 and LysgaY showed exolytic activity towards ~60% of the lactobacilli tested including four *L. fermentum* isolates from fuel ethanol fermentations. Presence of ethanol (≤5%) did not affect lytic activity. Lysins were able to reduce both *L. fermentum* and *L. reuteri* contaminants in mock fermentations of corn fiber hydrolysates. Recombinant LysA and λSa2 expressed in the yeast *Saccharomyces cerevisiae* are functional; LysA was shown to reduce lactobacilli in experimentally infected fermentations.

16 Claims, 5 Drawing Sheets
(4 of 5 Drawing Sheet(s) Filed in Color)

PEPTIDOGLYCAN HYDROLASE ANTIMICROBIALS FOR ERADICATING LACTOBACILLI THAT CONTAMINATE AND REDUCE ETHANOL YIELDS IN BIOFUEL FERMENTATION

BACKGROUND OF THE INVENTION

1. Field of the Invention

This invention relates to a method of using bacteriophage-encoded endolysins in the production of fuel alcohols by fermentation to control the growth of non-preferred, contaminating microorganisms such as *Lactobacillus* during fermentation. The LysA, LysA2, LysgaY and λSa2 endolysin constructs are active under fermentation conditions with regard to pH and presence of ethanol and lyse untreated, live lactobacilli in the fermentation cultures. LysA and λSa2 expressed in recombinant fermentation yeast *Saccharomyces cerevisiae* are functional and lyse lactobacilli in fermentation conditions.

2. Description of the Relevant Art

The fuel ethanol industry has experienced rapid growth in recent years, with 10.6 billion gallons produced in 2009 and future need estimated to be 60 billion gallons (340.69 billion liters) by 2030 in the United States alone. Currently, the majority of ethanol is produced from renewable carbohydrate-rich feedstock such as corn-starch or sugarcane, but to achieve higher demands in the future, lignocellulosic biomass will need to be utilized. Weakening the economics of biofuel production, are ethanol losses due to bacterial contamination of fermentation cultures. Contributing to this concern is the fact that it is not feasible to produce fuel ethanol under aseptic conditions, therefore chronic and acute contaminations are commonplace (Connolly, C. 1997. In: *The Alcohol Textbook*, 3rd Edition. Eds: Jacques et al., Nottingham University Press, pages 317-334; Skinner and Leathers. 2004. *J. Ind. Microbiol. Biotechnol.* 31: 401-408; Schell et al. 2007. *Bioresource Tech.* 98:2942-2948; Beckner et al. 2011. *Lett. Appl. Microbiol.* 53:387-394). A variety of Gram positive and Gram negative bacteria have been isolated from commercial fuel ethanol production facilities (Skinner and Leathers, supra; Beckner et al., supra; Bischoff et al. 2009. *Biotech. Bioengineer.* 103: 117-122). However, it is generally believed that lactic acid bacteria are the most detrimental, with *Lactobacillus* species predominating (Beckner et al., supra; Bischoff et al., supra; Limayem et al. 2011. *J. Environ. Science Health B* 46(8):709-714). Lactobacilli thrive in industrial fermentation environment because they are well adapted for survival under the high ethanol, low pH and low oxygen conditions. A major culprit, *L. fermentum*, has been shown to reduce ethanol production in *Saccharomyces cerevisiae* fermentation cultures by as much as 27% (Bischoff et al., supra; Chang et al. 1995. *J. Microbiol. Biotech.* 5:309-314). Controlling lactic acid bacteria in fermentation cultures often requires prophylactic antibiotic treatments and/or costly production shutdowns for extensive cleaning and disinfecting (Beckner et al., supra; Lushia and Heist. 2005. *Ethanol Producer Magazine* May: 80-82; Narendranath, N.V. In: *The Alcohol Textbook*, 4th Edition. 2003. Eds.: Jacques et al., Nottingham University Press, Nottingham, Pages 287-298). Despite current control measures and practices, long-term suppression of microbial contamination is still a major challenge in ethanol production.

There are numerous theories to account for the effect contaminants have on yeast during ethanol production. Chronic lactic acid bacteria contaminants are believed to compete for sugars available for conversion to ethanol as well as essential micronutrients required for optimal yeast growth. Acute contaminations often lead to the accumulation of major inhibitory end-products such as acetic and lactic acids that inhibit yeast growth and, if left untreated, cause "stuck" fermentations (Beckner et al., supra; Makanjuola et al. 1992. *Enzyme Microb. Tech.* 14:350-357; Narendranath et al. 1997. *Appl. Environ. Microbiol.* 63:4158-4163). Besides lowering the pH of the fermentation below the optimal *S. cerevisiae* pH range for the conversion of sugars to ethanol, the actual inhibitory impact of the acetic and lactic acid end products has been postulated to result from the undissociated form of the acid that is capable of diffusing through the yeast cell membrane where it dissociates, acidifying the yeast cytoplasm (Schnurer and Magnusson. 2005. *Trends Food Sci. Technol.* 16:70-78). Other compounds produced by lactic acid bacteria are known to contribute to the inhibition of ethanol production, for example, diacetyl (Lindgren and Dobrogosz. 1990. *FEMS Microbiol. Rev.* 7:149-163), fatty acids (Sjogren et al. 2003. *Appl. Environ. Microbiol.* 69:7554-7557) and the broad spectrum antibiotic reuterin (Schnurer and Magnusson, supra; Magnusson et al. 2003. *FEMS Microbiol. Lett.* 219:129-135).

Several techniques are currently being employed in an attempt to control microbial contaminants. In the United States, bacterial contaminants are commonly controlled with the commercially available antibiotics virginiamycin, penicillin, and erythromycin (Beckner et al., supra; Lushia and Heist, supra; Narendranath, N.V, supra). Treatment for contamination is often prophylactic, necessitating the addition of antibiotics to each fermentation cycle. However, decreased susceptibility to virginiamycin has already been observed in *Lactobacillus* species isolated from dry-grind ethanol plants that use virginiamycin (Demeester and Rondelet. 1976. *J. Antibiotics* 29:1297-1305), and the emergence of isolates with multidrug resistance to both virginiamycin and penicillin have also been reported (Lushia and Heist, supra; Bischoff et al. 2007. *J. Ind. Microbiol. Biotechnol.* 34:739-744). In addition, concerns over the potential for antibiotic residues to persist in the distillers grains co-products may further limit their use during ethanol production (McChesney, D. G. 2010. *FY 2010 Nationwide Survey of Distillers Grains for Antibiotic Residues*, US Food and Drug Administration). A 'no-antibiotic' approach has obvious advantages, but acceptable alternatives are currently lacking.

Bacteriophage (phage) endolysins are lytic enzymes produced by bacterial viruses. During phage infection of bacteria, lysins are produced near the end of the phage replication cycle to degrade peptidoglycan, (PG) (a major structural component of the bacterial cell wall), leading to cell lysis ('lysis from within') and phage progeny release (reviewed in Bernhardt et al. 2002. *Res. Microbiol.* 153:493-501). Scientists have found that externally lysin-treated Gram positive bacteria still lyse (exolysis or 'lysis from without'). Such exolysis has been exploited to control pathogenic and problematic bacteria (Loeffler et al. 2001. *Science* 294:2170-2172; Nelson et al. 2001. *Proc. Natl. Acad. Sci. USA* 98:4107-4112; Schuch et al. 2002. *Nature* 418:884-889; Schmelcher et al. 2012. *Appl. Environ. Microbiol.* 78:2297-2305). For review, see Nelson et al. 2012. *Adv. Virus. Res.* 83:299-365). Currently, such lysins are only considered exolytic for Gram positive bacteria because Gram negative bacteria have an outer membrane which prevents access of the lysin to the peptidoglycan of the Gram negative bacterial cell wall. However, Briers at al. and Lavigne at al. have reported using endolysin fusion proteins comprising peptides having membrane- or LPS-disrupting activity to facilitate endolysin activity (US2011/0243915 and US2012/0189606, respectively). Lysins exert their lethal effects by forming holes in the peptidoglycan. This degradation of the cells wall results in the extrusion of the cytoplasmic membrane due to the ~30 or 40 atm intracellular pressure resulting in osmolysis (Nelson et al., supra). Peptidoglycan is unique to bacteria and has a complex structure comprising a sugar backbone of alternating units of N-acetyl glucosamine and N-acetyl muramic acid (Schleifer and Kandler. 1972. *Bacteriol. Rev.* 36:407-477). Typically, these sugar polymers are cross-linked by species-specific oligopeptide attachments at the N-acetyl muramic acid residues (FIG. 1a). Phages have evolved lysins to be modular in design to compensate for peptidoglycan complexity, generally consisting of both lytic domains and cell wall binding (CWB) domains (FIG. 1b). Catalytically, a single lysin molecule should be sufficient to cleave an adequate number of bonds to lyse a bacterial call (Fischetti, V. A. 2010. *Int. J. Med. Microbiol.* 300:357-362).

There is a need for new specific antimicrobial treatments to control lactic acid bacterial contamination in fuel ethanol fermentations. We have identified *lactobacillus* bacteriophage endolysins which have exolytic activity towards ~60% of the lactobacilli tested, including four *L. fermentum* isolates from fuel ethanol fermentations.

SUMMARY OF THE INVENTION

We have discovered that LysA, LysA2, LysgaY and λSa2 endolysin constructs are highly exolytic against a variety of lactobacilli under laboratory conditions that mimic ethanol fermentation and that these endolysins can be used as an antimicrobial treatment to control unwanted lactobacilli contaminations in fermentation systems.

In accordance with this discovery, it is an object of the invention to provide a method of using these endolysin constructs as an effective and specific antimicrobial treatment to control unwanted lactobacilli contaminations in fermentation systems.

It is another object of the invention to provide a method of using LysA and λSa2 endolysin constructs having in particular a high lytic activity towards *L. fermentum*, a major contaminant of fermentation systems, as an effective and specific antimicrobial treatment to control unwanted lactobacilli contaminations in fermentation systems.

It is a further object of the invention to express the LysA, LysA2, LysgaY and λSa2 endolysin constructs in *S. cerevisiae* during a fermentation process directed to the production of alcohol, thus providing specific functional antimicrobial endolysins for the treatment to control unwanted lactobacilli contamination in the alcohol-producing fermentation system.

An added object of the invention is to provide a method of using LysA2 and LysgaY endolysin constructs as an effective and specific antimicrobial treatment to control unwanted *L. brevis* contaminants in late fermentations under conditions of increasing ethanol concentration.

It is a further object of the invention to provide a method of using LysA, LysA2, LysgaY and λSa2 endolysin constructs as an effective and specific antimicrobial treatment to control unwanted lactobacilli contaminations, such as *Lactobacillus amylovorus, L. brevis, L. delbrueckii, L. fermentum, L. gasseri*, and *L. reuteri* in fermentation systems.

An added object of the invention is to provide a method of using LysA2 endolysin constructs to control unwanted *L. casei* contaminants in fermentations systems.

Other objects and advantages of this invention will become readily apparent from the ensuing description.

BRIEF DESCRIPTION OF THE DRAWINGS

The patent or application file contains at least one drawing executed in color. Copies of this patent or patent application publication with color drawing(s) will be provided by the U.S. Patent and Trademark Office upon request and payment of the necessary fee.

FIG. 1a depicts a fragment of the repeat structure of *Lactobacillus fermentum* peptidoglycan with a D-Asp interpeptide bridge with the known enzymatic cut sites of λSa2 endolysin (1a); of λSa2 endolysin (3a); and of LysA2 (3b), and the predicted lysin catalytic sites (1b*) Lyb5, LysgaY, and LysA; and (2*) ABJ8901 [GenBank: ABJ63875] and BAG8101 [GenBank:BAG27815]. * Predicted catalytic sites are based on amino acid homologies to other biochemically determined enzymes. FIG. 1b depicts lysin architecture consisting of an enzymatically active domain(s) (square box) and cell wall binding domain(s) (hexagon box) drawn nearly to scale predicted using the NCBI Conserved Domain Database. A $His_6$-tag (dot box; not to scale) was fused on the C-terminal for metal ion affinity chromatography purification. The λSa2-ECC construct (SEQ ID NO:10) is a previously reported truncation of the λSa2 endolysin harboring just the N-terminal amidase-5 (pfam domain database) domain with a D-Glutaminyl-L-Lysine endopeptidase activity (FIG. 1a, 3a cut site) and the dual Cpl-7 cell wall binding domains (Donovan and Foster-Frey. 2008. *FEMS Microbiol. Lett.* 287:22-33).

FIG. 2a depicts SDS-PAGE: high intensity bands correspond to predicted molecular weights for endolysin constructs λSa2 endolysin (51.9 kD), LysgaY (33.9 kD), LysA2 (37.4 kD), and LysA (36.4 kD). FIG. 2b shows zymogram analysis with whole cell substrate (i) *Lactobacillus reuteri* 14171 and (ii) *Lactobacillus amylovorus* 4540, co-polymerized within the polyacrylamide gel. Lysin exolytic activity resulted in visible clearing (dark bands) of the cell substrate at the point of protein localization, which corresponds with predicted molecular weights.

FIG. 3a depicts the effect of pH on turbidity reduction specific activities ($OD_{600\ nm}$/min/μM) as described by Becker et al. (2008. *FEMS Microbiol. Lett.* 287:185-191). FIG. 3b shows the effect of ethanol on lysin activity (normalized to specific activity achieved at pH 5.5 in panel A). Live cells of *L. fermentum* 0605-B44 (blue), *L. fermentum* BR0315-1 (green), and *L. brevis* 0605-48 (red) were used as substrate. Data represents the average of three experiments (n=3) ±SEM.

FIG. 4a shows a hydrolysate inoculated with $1\times10^4$ CFU/ml *L. fermentum* isolate 0315-1 and treated with the λSA2 endolysin construct at 250 ng/μl (red), 75 ng/μl (green), 25 ng/μl (purple) and LysA construct at 25 ng/μl (blue). FIG. 4b depicts a hydrolysate inoculated with $1\times10^7$ CFU/ml *L. fermentum* isolate BR0315-1 and treated with 25 ng/μl (purple) λSA2 endolysin construct, PBS buffer control (black). FIG. 4c depicts a hydrolysate inoculated with $1\times10^4$ CFU/ml *L. reuteri* strain B-14171 and treated with LysA endolysin construct at 760 ng/μl (orange), PBS buffer control (black). Data represents the average of four plate counts (n=4)±SEM.

FIG. 5 depicts the expression of λSA2 endolysin and LysA constructs in *S. cerevisiae*. The genes for the each lysin were cloned in pYES-2.1 (Invitrogen, Carlsbad, Calif.), and transformed into *S. cerevisiae* INVSc1.

DETAILED DESCRIPTION OF THE INVENTION

Figure 1:
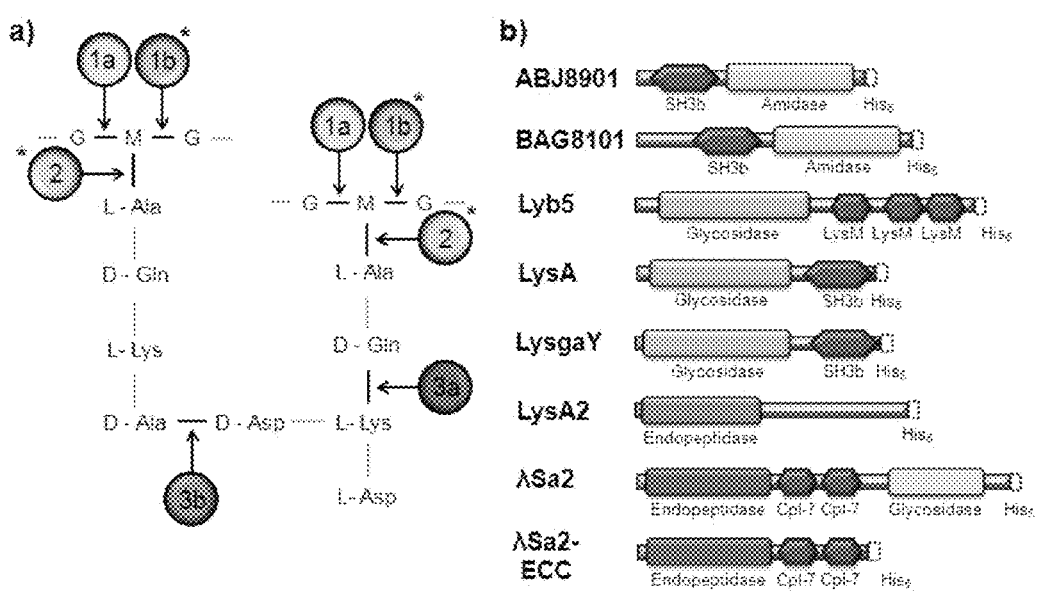
FIGS. 1a and 1b are schematic representations of peptidoglycan, putative lysin catalytic sites and domain structures of bacteriophage lysin constructs.

The goal was to identify bacteriophage lytic enzymes that can be used as antimicrobials toward Gram positive lactic acid bacteria known to contaminate fuel ethanol fermentations. From seven putative lysin genes, we have identified four recombinant phage lysins, LysA, LysA2, LysgaY and λSa2 endolysin, (Turner et al. 2004. *FEMS Microbiol. Lett.* 238:9-15; Ribelles et al. 2012. *Appl. Microbiol. Biotechnol.* 94:101-110; Yokoi et al. 2005. *Int. J. Food Microbiol.* 99:297-308; Pritchard et al. 2007. *Appl. Environ. Microbiol.* 73:7150-7154; and Donovan and Foster-Frey. 2008. *FEMS Microbiol. Lett.* 287:22-33) that show high activity against lactic acid bacteria contaminants from fuel ethanol fermentations. These enzymes have broad exolytic activity in vitro towards numerous Gram positive lactic acid bacteria including several fermentation isolates of *L. fermentum*. Although LysA (SEQ ID NO: 2), LysA2 (SEQ ID NO: 4), LysgaY (SEQ ID NO: 6) and λSa2 (SEQ ID NO: 8) endolysin constructs all demonstrated exolytic activity against lactobacilli, the lactobacilli lysin LysA and the streptococcal λSa2 phage endolysin constructs showed the greatest efficacies to reduce populations of *L. fermentum*. Interestingly, the streptococcal λSa2 endolysin also exhibited the broadest lytic activity towards the lactic acid bacteria and other Gram positive bacteria we tested.

It is virtually impossible to avoid lactic acid bacteria contaminations in fuel ethanol fermentations; and therefore, the risk of reduced ethanol yield is a major concern. The most common commercially available products used to control contamination in fuel ethanol facilities are based on the antibiotics virginiamycin and penicillin (Connolly, supra; Lushia and Heist, supra) where the recommended dosing range in fuel ethanol fermentations is generally 0.25-2.0 ppm (Narendranath, supra) which makes the fuel ethanol industry one of the largest consumers of antibiotics. However, the emergence of antibiotic resistant *Lactobacillus* has occurred in fuel ethanol production facilities (Lushia and Heist, supra; Bischoff et al. 2007, supra). Phage lysins can avoid many resistance pitfalls associated with antibiotic use. Typically antibiotic resistance is a consequence of a bacterial mutation or acquisition of genes that improve the fitness of the recipient bacterium allowing it to evade the action of antibiotics. These adaptations generally occur inside the bacterial cell and employ three general strategies: modification of the drug, alteration of the target (or its level of expression), or decreased accessibility of the drug to its target (reviewed by Bischoff et al. 2004. In: *Preharvest and Postharvest Food safety: Contemporary Issues and Future Directions*. Eds.: Beier et al., Blackwell Publishing Professional, pages 201-212); whereas, phage lysins target the peptidoglycan, which is located outside the cytoplasmic membrane and reduce the number of possible known mechanisms by which bacterial resistance typically emerges (Spratt, B. G. 1994. *Science* 264:388-393). The near-species specificity of phage lysins also avoids many pitfalls associated with broad-spectrum antimicrobial treatments. Broad-spectrum antimicrobials lead to selection for resistant strains, not just in the target pathogen, but also in co-resident bacteria exposed to the drug, due to the acquisition of resistance genes. These strains that are antibiotic resistant can serve as carriers of these DNA elements during future treatment episodes. Phage lysins are a relatively new class of antimicrobials. Despite repeated attempts, no strains of host bacteria that can resist the lytic activities of their bacteriophage endolysins have been reported (Schuch et al. 2002, supra; Loeffler et al. 2001, supra (reviewed in: Fischetti, V. A. 2005. *Trends Microbiol.* 13:491-496). It is possible that the phages and bacteria have co-evolved such that the phages have selected immutable peptidoglycan bonds that it targets with the endolysin in order to guarantee escape from the bacterium. Similarly, peptidoglycan hydrolases are non-toxic, non-caustic, biodegradable, and also kill bacteria in biofilms, an important consideration for many health and biotechnology applications (Sass and Bierbaum. 2007. *Appl. Environ. Microbiol.* 73:347-352).

Lysins are currently being used as disinfectants in industrial settings. Lysozyme which is isolated from hen egg albumen is also a peptidoglycan hydrolytic enzyme similar to phage encoded lysins. It has been found to be useful in controlling unwanted bacteria in wines at concentrations of 250-500 mg/l (Gerbouz et al. 1997. *Am. J. Enol. Vitic.* 48:49-54). Although lysozyme has been found to inhibit undesirable malolactic fermentation by *Oenococcos oeni*, strains of pediococci and lactobacilli, which are usually blamed for serious defects in musts and wines, were resistant (Delfini et al. 2004. *J. Agric. Food Chem.* 52:1861-1866). Bacteria are also known to produce various peptidoglycan hydrolases; for example, a *Streptomyces* strain produces a mixture of muramidases and proteases that are secreted into the medium. When collected, this mixture has shown broad lytic activity against a variety of wine-relevant lactic acid bacteria; however, lytic activity on *L. fermentum* was not tested (Blattel et al. 2009. *Appl. Microbiol. Biotechnol.* 83:839-848) and therefore it is uncertain if this approach could be used in a fuel ethanol fermentation system. Other examples for the potential use of lysin-based environmental disinfectants include lysins PlyC (from the streptococcal bacteriophage C$_1$ [phage lysin from C$_1$]) and Lysostaphin (Hoopes at al. 2009. *Appl. Environ. Microbiol.* 75:1388-1394). PlyC was found to be 1,000 fold more active on a per weight basis than commercially available oxidizing disinfectants and was shown to retain effectiveness when tested in the presence of non-ionic detergents, hard water, and organic material (Hoopes et al., supra). The staphylococcal lysin lysostaphin, a peptidoglycan hydrolase bacteriocin, has been shown to be effective in killing methicillin-resistant *S. aureus* (MRSA) on solid surfaces (Graham and Coote. 2007. *J. Antimicrob. Chemother.* 59:759-762). Therefore, the study of phage encoded lytic enzymes with activity against problematic lactic acid bacteria in fuel ethanol fermentations is highly relevant and needed.

The differences we observed in exolytic activity of the four lysins against different species (Table 2), is possibly reflected in compositional changes in the cell walls between them. Of the three lactobacilli lysins tested, the exact cut site has only been experimentally determined for LysA2. LysA2 cleaves the bond between the bridging aspartic acid and the final D-alanine of one of the tetrapeptides involved in the binding of adjacent peptidoglycan chains of *L. casei* (FIG. 1*b*) (Ribelles et al., supra). This particular architecture is typical of lactobacilli as well as many other lactic acid bacteria, including the pediococci (Schleifer and Kandler, supra). However, some lactobacilli were only moderately exolysed by LysA2, for example, *L. fermentum, L. reuteri*, and *L. gasseri*, while others, e.g., *L. debrueckii, L. malefermentans, L paracasei*, were not sensitive to the lysin. A plausible explanation for this lysin specificity could be derived from the cell wall binding domain. Certain *Listeria monocytogenes* lysins have cell wall binding domains that specifically recognize and bind to teichoic acids before degradation of the peptidoglycan can occur (Eugster et al. 2011. *Mol. Microbiol.* 81:1419-1432). For the lysins tested here, it is not known if and how the cell wall binding domains are interacting with the cell wall binding to or the prevalence of potential epitopes on the cell surface of the lactic acid bacteria tested here. Similarly, ethanol stresses on the cell wall (FIG. 3*b*) or phase of growth (logarithmic, stationary, or biofilm) may contribute significantly to sensitivity to endolysins, although endolysins are generally believed to be active on all phases of cell growth.

It is interesting that the streptococcal enzyme, λSa2 prophage endolysin, is our strongest candidate antimicrobial for lactobacilli. The most likely explanation for this cross-genera activity is that both of the λSa2 endolysin lytic domains target the *Lactobacillus* peptidoglycan. The C-terminal N-acetylglucosaminidase cleaves the glycan component of the peptidoglycan on the reducing side of GlcNAc (FIG. 1*a*) (Pritchard et al., supra). The N-terminal λSa2 endolysin catalytic domain harbors a D-glutaminyl-L-lysine endopeptidase activity, which cleaves the peptide bonds between two amino acids D-glutamine and L-lysine (Pritchard et al., supra). This exact sequence is present in most lactobacilli peptidoglycan, and is reported in 1 strain of *L. fermentum* in 1972 (FIG. 1*a*), but is replaced with L-ornithine at the third position of the tetrapeptide in the peptidoglycan of most *L. fermentum* (Schleifer and Kandler, 1972), the species where λSa2 endolysin is apparently most active (Table 2). Although we have no biochemical data to indicate that the N-terminal λSa2 endolysin endoopeptidase domain is cutting at this L-gluaminyl-L-ornithine bond, we have shown that a previously described (Donovan and Foster-Frey 2008, supra) truncated version of the λSa2 endolysin harboring just this endopeptidase domain and two Cpl-7 cell wall binding domains (λSa2-ECC; FIG. 1*b*), is lytic for *L. fermentum* (Table 2). Considering the similarity between L-lysine and L-ornithine (lysine harbors 4 carbons in the amino terminal alkyl side chains, rather than 3 for ornithine), it is thus most likely that this domain is cutting the peptidoglycan at the L-glutamine-L-ornithine bond. In support of this possibility is the fact that LysA2 endopeptidase activity, the activity where the bond between the terminal D-alanine of the peptidoglycan tetrapeptide and the D-aspartic acid residue that forms the bridge with the L-lysine of a neighboring peptidoglycan chain is hydrolyzed, was reported to function on species that harbor either an L-lysine or an L-ornithine at position three in the neighboring tetrapeptide (Ribelles et al., supra). Although not a definitive or even a direct comparison, this suggests a degree of flexibility in the recognition sequences surrounding the cut site of these peptidoglycan hydrolase lytic domains. Alternatively, all of the *L. fermentum* isolates that were lysed with the λSa2-ECC in Table 2 might harbor L-lysine rather than L-ornithine at position 3 of the stem peptide, as was reported a possibility by Schliefer and Kandler, 1972.

It is interesting to speculate on whether or not sensitivity to ethanol will be a significant factor in the efficacy of the lytic enzymes we have tested. Although final fermentation conditions yield ethanol concentrations greater than 5%, the starting feedstock is a major culprit for introducing lactic acid bacterial contamination to the fermentation system (Schell et al., supra), a point at which the fermentation is highly sensitive to contamination (Russel, I. 2003. In: *The Alcohol Textbook* $4^{th}$ *Edition*. Eds: Jadanova et al., pages 85-119). It is this initial stage in the fermentation where there is minimal ethanol concentration that would be ideal for lysin treatment; thereby removing ethanol as a factor. Certainly enzymes that have a broad range of activity regardless of ethanol concentration might provide a longer-lived protection during the fermentation process, especially if they are designed to be secreted from recombinant fermentative yeast throughout the fermentation process. However, it has yet to be determined if a broader species-target range or biochemical resilience under ethanolic fermentation conditions is more important for the optimal antimicrobial when considering the complex environment of a lignocellulosic fermentation. The increased activity of LysA2 and LysgaY constructs against *L. brevis* with increasing ethanol concentration is intriguing and suggests these might be preferred enzymes if treating *L. brevis* contaminants in late fermentations.

Our studies indicate that LysA, LysA2, LysgaY and λSa2 endolysin constructs are excellent antibacterial agents and candidates for use in fermentation environments and that the LysA and λSa2 endolysin genes when expressed in recombinant fermentative yeast result in functional lysins that are effective for lysing lactobacilli in a fermentation. By homology screening of these lysins to other known peptidoglycan hydrolase lytic and cell wall binding domains, there is no shortage of phage lysins for future consideration, as public datasets contain numerous putative lytic peptidoglycan hydrolases from both bacterial (prophage) and phage genome origins. Due to the high interest in phages that impinge on yogurt production, there are literally hundreds of known lactobacilli phage, with nine complete *Lactobacillus* phage genomes and 11 *Lactobacillus* poly-lysogenic bacterial genomes with sequence available on the NCBI website (Villion and Moineau. 2009. *Front Biosci.* 14:1661-1683). For example, lactobacilli lysins from ϕadh (Henrich et al. 1995. *J. Bacteriol.* 177:723-732) and Φg1e (Oki et al. 1996. *Gene* 176:215-223; Kakikawa et al. 2002. *Gene* 299:227-234) have been shown to be functional lytic enzymes, although their ability to exolyse cells has not been reported. There is also a report of an amidase domain from the PL-1 phage endolysin that infects *L. casei* (Kashige et al. 2000. *Arch. Virol.* 145: 1521-1534) and a muramidase (Mur-LH) that have shown a broad species lytic activity (Deutsch et al. 2004. *Appl. Environ. Microbiol.* 70:96-103). However, due to limitations in the species range of lytic activity, each candidate will need to be tested empirically against target lactic acid bacteria.

Our most broadly effective enzymes, λSa2 endolysin and LysA, have been tested in mock fermentations and shown to effectively reduce the lactic acid bacteria load by up to 2 orders of magnitude. These initial trials do not necessarily reflect normal fermentation conditions; in order to easily detect changes in target contaminant profiles, the mock trial was performed under pre-sterilization conditions, such that the only contaminant was *L. fermentum*, an unlikely scenario in industrial fermentations. Also, neither the yeast nor the lactic acid bacteria were adapted for growth on hydrolysate; rather, they were both grown in rich broth and then added to the hydrolysate. This assay was designed to test the enzymes for activity under hydrolysate conditions, the results of which are encouraging, but activity on the contaminant might be affected by the cell wall of the contaminant during hydrolysate growth conditions.

Although expected, due to the absence of peptidoglycan in yeast cell walls, it should also be noted that none of these lysins including λSa2 endolysin had any catalytic activity towards *S. cerevisiae* when applied externally; therefore, they would not be expected to adversely affect the fermentation process. In addition, the heat of distillation and the heat of drying the distiller's grains should denature the lysins, minimizing any potential impact on gut microflora of animals fed the ethanol co-products. Therefore, lysins appear to share qualities worth considering for future works to protect ethanolic fermentations from lactic acid bacteria contaminants.

We demonstrate that LysA and λSa2 endolysin are highly exolytic against a variety of lactobacilli, under laboratory conditions that mimic ethanol fermentation environments, with high lytic activity observed towards *L. fermentum*. These results indicate that lysins have potential application to control unwanted lactobacilli contaminations in fermentation systems.

According to the present invention, the terms "nucleic acid molecule", "nucleic acid sequence", "polynucleotide", "polynucleotide sequence", "nucleic acid fragment", "isolated nucleic acid fragment" are used interchangeably herein. These terms encompass nucleotide sequences and the like. A polynucleotide may be a polymer of RNA or DNA that is single- or double-stranded and that optionally contains synthetic, non-natural or altered nucleotide bases. A polynucleotide in the form of a polymer of DNA may be comprised of one or more segments of cDNA, genomic DNA, synthetic DNA, or mixtures thereof. This will also include a DNA sequence for which the codons encoding the LysA, LysA2, LysgaY and/or λSa2 endolysin constructs according to the invention will have been optimized according to the host organism in which it will be expressed, these optimization methods being well known to those skilled in the art.

The term "isolated" polynucleotide refers to a polynucleotide that is substantially free from other nucleic acid sequences, such as other chromosomal and extrachromosomal DNA and RNA, that normally accompany or interact with it as found in its naturally occurring environment. However, isolated polynucleotides may contain polynucleotide sequences which may have originally existed as extrachromosomal DNA but exist as a nucleotide insertion within the isolated polynucleotide. Isolated polynucleotides may be purified from a host cell in which they naturally occur. Conventional nucleic acid purification methods known to skilled artisans may be used to obtain isolated polynucleotides. The term also embraces recombinant polynucleotides and chemically synthesized polynucleotides.

The term "transgene" is understood to describe genetic material which has been or is about to be artificially inserted into the genome of a non-human animal, and particularly into a cell of a living non-human mammal. It is to be understood that as used herein the term "transgenic" includes any cell, cell line, or tissue, the genotype of which has been altered by the presence of a heterologous nucleic acid including those transgenics initially so altered as well as those created by sexual crosses or asexual propagation from the initial transgenic.

The term "transformation" refers to a permanent or transient genetic change induced in a cell following the incorporation of new DNA (i.e. DNA exogenous to the cell). Where the cell is a mammalian cell, a permanent genetic change is generally achieved by introduction of the DNA into the genome of the cell. When the cell is a bacterial cell, the term usually refers to an extrachromosomal, self-replicating vector which harbors a selectable antibiotic resistance. Thus, isolated polynucleotides of the present invention can be incorporated into recombinant constructs, typically DNA constructs, capable of introduction into and replication in a host cell. Such a construct can be a vector that includes a replication system and sequences that are capable of transcription and translation of a polypeptide-encoding sequence in a given host cell.

The term "construct" refers to a recombinant nucleic acid, generally recombinant DNA, that has been generated for the purpose of the expression of a specific nucleotide sequence(s), or is to be used in the construction of other recombinant nucleotide sequences. A "construct" or "chimeric gene construct" refers to a nucleic acid sequence encoding a protein, operably linked to a promoter and/or other regulatory sequences.

The term "operably linked" refers to the association of two or more nucleic acid fragments on a single nucleic acid fragment so that the function of one is affected by the other. For example, a promoter is operably linked with a coding sequence when it is capable of affecting the expression of that coding sequence (i.e., that the coding sequence is under the transcriptional control of the promoter) or a DNA sequence and a regulatory sequence(s) are connected in such a way as to permit gene expression when the appropriate molecules (e.g., transcriptional activator proteins) are bound to the regulatory sequence(s).

"Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence.

"Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence that can stimulate promoter activity and may be an innate element of the promoter or a heterologous element inserted to enhance the level or tissue-specificity of a promoter.

The term "cDNA" refers to all nucleic acids that share the arrangement of sequence elements found in native mature mRNA species, where sequence elements are exons and 3' and 5' non-coding regions. Normally mRNA species have contiguous exons, with the intervening introns removed by nuclear RNA splicing, to create a continuous open reading frame encoding the protein. "cDNA" refers to a DNA that is complementary to and derived from an mRNA template.

The term "genomic sequence" refers to a sequence having non-contiguous open reading frames, where introns interrupt the protein coding regions. It may further include the 3' and 5' untranslated regions found in the mature mRNA. It may further include specific transcriptional and translational regulatory sequences, such as promoters, enhancers, etc., including about 1 kb, but possibly more, of flanking genomic DNA at either the 5' or 3' end of the transcribed region. The genomic DNA may be isolated as a fragment of 100 kbp or smaller; and substantially free of flanking chromosomal sequence.

As used herein, "recombinant" refers to a nucleic acid molecule which has been obtained by manipulation of genetic material using restriction enzymes, ligases, and similar genetic engineering techniques as described by, for example, Sambrook et al. 1989. Molecular Cloning: A Laboratory Manual, Second Edition, Cold Spring Harbor Laboratory Press, Cold Spring Harbor, N.Y. or DNA Cloning: A Practical Approach, Vol. I and II (Ed. D. N. Glover), IRL Press, Oxford, 1985. "Recombinant," as used herein, does not refer to naturally occurring genetic recombinations.

As used herein, the term "chimeric" refers to two or more DNA molecules which are derived from different sources, strains, or species, which do not recombine under natural conditions, or to two or more DNA molecules from the same species, which are linked in a manner that does not occur in the native genome.

As used herein, the terms "encoding", "coding", or "encoded" when used in the context of a specified nucleic acid mean that the nucleic acid comprises the requisite information to guide translation of the nucleotide sequence into a specified protein. The information by which a protein is encoded is specified by the use of codons. A nucleic acid encoding a protein may comprise non-translated sequences (e.g., introns) within translated regions of the nucleic acid or may lack such intervening non-translated sequences (e.g., as in cDNA).

A "protein" or "polypeptide" is a chain of amino acids arranged in a specific order determined by the coding sequence in a polynucleotide encoding the polypeptide. Each protein or polypeptide has a unique function.

The invention includes functional LysA, LysA2, LysgaY and λSa2 endolysin polypeptide and functional fragments thereof, as well as mutants and variants having the same biological function or activity. As used herein, the terms "functional fragment", "mutant" and "variant" refers to a polypeptide which possesses biological function or activity identified through a defined functional assay and associated with a particular biologic, morphologic, or phenotypic alteration in the cell. The term "functional fragments of LysA, LysA2, LysgaY and/or λSa2 endolysin" refers to all fragments of LysA, LysA2, LysgaY and/or λSa2 endolysin that retain LysA, LysA2, LysgaY and/or λSa2 endolysin activity and function to lyse contaminating bacteria in fermentation (See Table 2).

Modifications of the LysA, LysA2, LysgaY and/or λSa2 endolysin primary amino acid sequence may result in further mutant or variant proteins having substantially equivalent activity to the LysA, LysA2, LysgaY and/or λSa2 endolysin polypeptides described herein. Such modifications may be deliberate, as by site-directed mutagenesis, or may occur by spontaneous changes in amino acid sequences where these changes produce modified polypeptides having substantially equivalent activity to the LysA, LysA2, LysgaY and/or λSa2 endolysin polypeptide. Any polypeptides produced by minor modifications of the LysA, LysA2, LysgaY and/or λSa2 endolysin primary amino acid sequence are included herein as long as the biological activity of LysA, LysA2, LysgaY and/or λSa2 endolysin is present; e.g., having a role in pathways leading to lysis of streptococci or lactobacilli.

As used herein, "substantially similar" refers to nucleic acid fragments wherein changes in one or more nucleotide bases results in substitution of one or more amino acids, but do not affect the functional properties of the polypeptide encoded by the nucleotide sequence. "Substantially similar" also refers to modifications of the nucleic acid fragments of the instant invention such as deletion or insertion of nucleotides that do not substantially affect the functional properties of the resulting transcript. It is therefore understood that the invention encompasses more than the specific exemplary nucleotide or amino acid sequences and includes functional equivalents thereof. Alterations in a nucleic acid fragment that result in the production of a chemically equivalent amino acid at a given site, but do not affect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products. A method of selecting an isolated polynucleotide that affects the level of expression of a polypeptide in a host cell may comprise the steps of constructing an isolated polynucleotide of the present invention or an isolated chimeric gene of the present invention; introducing the isolated polynucleotide or the isolated chimeric gene into a host cell; measuring the level of a polypeptide in the host cell containing the isolated polynucleotide; and comparing the level of a polypeptide in the host cell containing the isolated polynucleotide with the level of a polypeptide in a host cell that does not contain the isolated polynucleotide.

Moreover, substantially similar nucleic acid fragments may also be characterized by their ability to hybridize. Estimates of such homology are provided by either DNA-DNA or DNA-RNA hybridization under conditions of stringency as is well understood by those skilled in the art (1985. *Nucleic Acid Hybridization,* Hames and Higgins, Eds., IRL Press, Oxford, U.K.). Stringency conditions can be adjusted to screen for moderately similar fragments, such as homologous sequences from distantly related organisms, to highly similar fragments, such as genes that duplicate functional enzymes from closely related organisms. An indication that nucleotide sequences are substantially identical is if two molecules hybridize to each other under stringent conditions. Generally, stringent conditions are selected to be about 5° C. lower than the thermal melting point (Tm) for the specific sequence at a defined ionic strength and pH. However, stringent conditions encompass temperatures in the range of about 1° C. to about 20° C., depending upon the desired degree of stringency as otherwise qualified herein. Thus, isolated sequences that encode a LysA, LysA2, LysgaY and/or λSa2 endolysin polypeptide and which hybridize under stringent conditions to the LysA, LysA2, LysgaY and/or λSa2 endolysin sequences disclosed herein, or to fragments thereof, are encompassed by the present invention.

Substantially similar nucleic acid fragments of the instant invention may also be characterized by the percent identity of the amino acid sequences that they encode to the amino acid sequences disclosed herein, as determined by algorithms commonly employed by those skilled in this art. Methods of alignment of sequences for comparison are well known in the art. Thus, the determination of percent identity between any two sequences can be accomplished using a mathematical algorithm. Non-limiting examples of such mathematical algorithms are the algorithm of Myers and Miller (1988. *CABIOS* 4:11-17), the local homology algorithm of Smith et al. (1981. *Adv. Appl. Math.* 2:482); the homology alignment algorithm of Needleman and Wunsch (1970. *J. Mol. Biol.* 48:443-453); the search-for-similarity-method of Pearson and Lipman (1988. *Proc. Natl. Acad. Sci.* 85:2444-2448; the algorithm of Karlin and Altschul (1990. *Proc. Natl. Acad. Sci. USA* 87:2264), modified as in Karlin and Altschul (1993. *Proc. Natl. Acad. Sci. USA* 90:5873-5877).

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters.

As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins, it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule.

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

The term "substantial identity" of polynucleotide sequences means that a polynucleotide comprises a sequence that has at least 80% sequence identity, preferably at least 85%, more preferably at least 90%, most preferably at least 95% sequence identity compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 80%, preferably at least 85%, more preferably at least 90%, and most preferably at least 95%. Preferably, optimal alignment is conducted using the homology alignment algorithm of Needleman et al. (1970. *J. Mol. Biol.* 48:443).

A "substantial portion" of an amino acid or nucleotide sequence comprises an amino acid or a nucleotide sequence that is sufficient to afford putative identification of the protein or gene that the amino acid or nucleotide sequence comprises. Amino acid and nucleotide sequences can be evaluated either manually by one skilled in the art, or by using computer-based sequence comparison and identification tools that employ algorithms such as BLAST. In general, a sequence of ten or more contiguous amino acids or thirty or more contiguous nucleotides is necessary in order to putatively identify a polypeptide or nucleic acid sequence as homologous to a known protein or gene. Moreover, with respect to nucleotide sequences, gene-specific oligonucleotide probes comprising 30 or more contiguous nucleotides may be used in sequence-dependent methods of gene identification and isolation. In addition, short oligonucleotides of 12 or more nucleotides may be use as amplification primers in PCR in order to obtain a particular nucleic acid fragment comprising the primers. Accordingly, a "substantial portion" of a nucleotide sequence comprises a nucleotide sequence that will afford specific identification and/or isolation of a nucleic acid fragment comprising the sequence. The instant specification teaches amino acid and nucleotide sequences encoding polypeptides that comprise a particular plant protein. The skilled artisan, having the benefit of the sequences as reported herein, may now use all or a substantial portion of the disclosed sequences for purposes known to those skilled in this art. Thus, such a portion represents a "substantial portion" and can be used to establish "substantial identity", i.e., sequence identity of at least 80%, compared to the reference sequence. Accordingly, the instant invention comprises the complete sequences as reported in the accompanying Sequence Listing, as well as substantial portions at those sequences as defined above.

Fragments and variants of the disclosed nucleotide sequences and proteins encoded thereby are also encompassed by the present invention. By "fragment" a portion of the nucleotide sequence or a portion of the amino acid sequence and hence protein encoded thereby is intended. Fragments of a nucleotide sequence may encode protein fragments that retain the biological activity of the native protein and hence have LysA, LysA2, LysgaY and/or λSa2 endolysin-like activity. Alternatively, fragments of a nucleotide sequence that are useful as hybridization probes may not encode fragment proteins retaining biological activity.

By "variants" substantially similar sequences are intended. For nucleotide sequences, conservative variants include those sequences that, because of the degeneracy of the genetic code, encode the amino acid sequence of one of the LysA, LysA2, LysgaY and/or λSa2 endolysin polypeptides of the invention. Naturally occurring allelic variants such as these can be identified with the use of well-known molecular biology techniques, as, for example, with polymerase chain reaction (PCR), a technique used for the amplification of specific DNA segments. Generally, variants of a particular nucleotide sequence of the invention will have generally at least about 90%, preferably at least about 95% and more preferably at least about 98% sequence identity to that particular nucleotide sequence as determined by sequence alignment programs described elsewhere herein.

By "variant protein" a protein derived from the native protein by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein is intended. Variant proteins encompassed by the present invention are biologically active, that is they possess the desired biological activity, that is, LysA, LysA2, LysgaY and/or λSa2 endolysin activity as described herein. Such variants may result from, for example, genetic polymorphism or from human manipulation. Biologically active variants of a native LysA, LysA2, LysgaY and/or λSa2 endolysin protein of the invention will have at least about 90%, preferably at least about 95%, and more preferably at least about 98% sequence identity to the amino acid sequence for the native protein as determined by sequence alignment programs described elsewhere herein. A biologically active variant of a protein of the invention may differ from that protein by as few as 1-15 amino acid residues, or even 1 amino acid residue.

The polypeptides of the invention may be altered in various ways including amino acid substitutions, deletions, truncations, and insertions. Novel proteins having properties of interest may be created by combining elements and fragments of proteins of the present invention, as well as with other proteins. Methods for such manipulations are generally known in the art. Thus, the genes and nucleotide sequences of the invention include both the naturally occurring sequences as well as mutant forms. Likewise, the proteins of the invention encompass naturally occurring proteins as well as variations and modified forms thereof. Such variants will continue to possess the desired LysA, LysA2, LysgaY and/or λSa2 endolysin activity. Obviously, the mutations that will be made in the DNA encoding the variant must not place the sequence out of reading frame and preferably will not create complementary regions that could produce secondary mRNA structure.

The deletions, insertions, and substitutions of the protein sequences encompassed herein are not expected to produce radical changes in the characteristics of the protein. However, when it is difficult to predict the exact effect of the substitution, deletion, or insertion in advance of doing so, one skilled in the art will appreciate that the effect will be evaluated by routine screening assays where the effects of LysA, LysA2, LysgaY and/or λSa2 endolysin protein can be observed.

"Codon degeneracy" refers to divergence in the genetic code permitting variation of the nucleotide sequence without affecting the amino acid sequence of an encoded polypeptide. Accordingly, the instant invention relates to any nucleic acid fragment comprising a nucleotide sequence that encodes all or a substantial portion of the amino acid sequences set forth herein.

Avoiding the generalized use of broad range antimicrobials and using highly specific antimicrobials for just the target organisms involved, should help reduce the ever-increasing incidence of antibiotic resistant strain development.

EXAMPLES

Having now generally described this invention, the same will be better understood by reference to certain specific examples, which are included herein only to further illustrate the invention and are not intended to limit the scope of the invention as defined by the claims.

Example 1

Constructs, Strains, and Plasmids

The lysins that were bioinformatically selected and synthesized or obtained for use in this study are listed in Table 1. LysA, LysA2, LysgaY genes were bioinformatically reverse translated with an *E. coli* codon bias and gene nucleotide sequences were commercially synthesized and cloned into pUC57 vector (GenScript, Piscataway, N.J.). The *Streptococcus agalactiae* phage lysin λSa2 (EMD Biosciences, San Diego, Calif.) was obtained as a gift from Pritchard et al., supra. LysA, LysA2, LysgaY genes were subcloned into the pET21a *E. coli* expression vector (EMD Biosciences, San Diego, Calif.), which adds an XhoI restriction enzyme site and 6×His codons at the 3' end of the coding sequences (resulting in LEHHHHHH added to the N-terminus of the native protein). The plasmids were maintained in *E. coli* DH5α (Invitrogen, Carlsbad, Calif.) at 37° C. in LB medium supplemented with 150 μg/ml ampicillin for plasmid purification, maintenance and DNA sequence verification.

TABLE 1

Lysins bioinformatically selected from GenBank for cloning into pET21a protein expression vector.

| Lysin | Origin | Reference or Source |
|---|---|---|
| ABJ8901 | *Lactobacillus brevis* ATCC367 | GenBank: ABJ63875 |
| BAG8101 | *Lactobacillus fermentum* IFO 3956 | GenBank: BAG27815 |
| Lyb5 | *Lactobacillus fermentum* phage ΦPBY5 | Wang et al., supra |
| LysA | *Lactobacillus fermentum* Br11 | Turner et al., supra |
| LysA2 | *Lactobacillus casei* phage ΦA2 | Ribelles et al., supra |
| LysgaY | *Lactobacillus fermentum* phage ΦgaY | Yokoi et al., supra |
| λSa2 endolysin | *Streptococcus agalactiae* | Pritchard et al., supra |

The bacterial strains used and their origin are listed in Table 2. Staphylococci and streptococci were grown in Tryptic Soy Broth (TSB; Difco Laboratories) medium with shaking at 37° C., *E. coli* was grown in Luria-Bertani (LB; Difco Laboratories) medium broth at 37° C. with shaking, and lactobacilli were grown in de Man, Rogosa and Sharp (MRS; Difco Laboratories) medium at 37° C. without shaking. *S. cerevisiae* was grown overnight in yeast extract peptone (YP; Becton, Dickinson, and Co. Sparks, Md.) medium supplemented with 4% (w/v) glucose at 30° C. with shaking.

TABLE 2

Activity of LysA, LysA2, LysgaY, λSa2 and truncated λSa2 endolysin (λSa2-ECC) against lactic acid bacteria as determined by turbidity ($OD_{600\ nm}$) reduction analysis.

| | Activity[a] | | | | | |
|---|---|---|---|---|---|---|
| Strain | LysA | LysA2 | LysgaY | λSa2 | λSa2-ECC[h] | Strain Source |
| Gram positive | | | | | | |
| *Lactobacillus amylovorus* B-4540 | − | ++ | ++ | ++ | NT[g] | NRRL[b] |
| *Lactobacillus brevis* 0605-48 | ++ | ++ | ++ | ++ | + | this study[c] |

TABLE 2-continued

Activity of LysA, LysA2, LysgaY, λSa2 and truncated λSa2 endolysin (λSa2-ECC) against lactic acid bacteria as determined by turbidity ($OD_{600\ nm}$) reduction analysis.

| Strain | Activity[a] | | | | | Strain Source |
|---|---|---|---|---|---|---|
| | LysA | LysA2 | LysgaY | λSa2 | λSa2-ECC[h] | |
| *Lactobacillus delbrueckii* subsp *delbrueckii* B-763 | − | − | + | + | NT | NRRL |
| *Lactobacillus fermentum* BRO315-1 | ++ | + | + | ++ | NT | this study |
| *Lactobacillus fermentum* BRO315-25 | ++ | + | + | +++ | + | this study |
| *Lactobacillus fermentum* 0605-B44 | +++ | + | + | +++ | + | this study |
| *Lactobacillus fermentum* 0713-3 | +++ | + | + | +++ | NT | this study |
| *Lactobacillus gasseri* B-4240 | +++ | + | + | +++ | NT | NRRL |
| *Lactobacillus hilgardii* B-1843 | − | − | − | − | NT | NRRL |
| *Lactobacillus malefermentans* B-1861 | − | − | − | ++ | NT | NRRL |
| *Lactobacillus paracasei* BRO315-44 | − | − | − | − | NT | this study |
| *Lactobacillus reuteri* B-14171 | ++ | + | ++ | + | NT | NRRL |
| *Staphylococcus aureus* Newman | + | − | + | +++ | +[h] | Jean C. Lee[d] |
| *Staphylococcus epidermidis* | + | − | ++ | +++ | NT | USDA |
| *Staphylococcus hyicus* | − | − | − | + | −[h] | USDA |
| *Staphylococcus warneri* | + | − | + | +++ | −[h] | USDA |
| *Staphylococcus xylocus* | ++ | − | ++ | +++ | +[h] | USDA |
| *Streptococcus agalactiae* | ++ | − | ++ | +++ | ++[h] | D. Pritchard[e] |
| *Streptococcus dysgalactiae* | ++ | − | ++ | +++ | +++[h] | USDA |
| *Streptococcus pyogenes* | + | − | + | +++ | +++[h] | D. Nelson[f] |
| *Streptococcus suis* 531-668 | +++ | − | +++ | +++ | NT | D. Nelson[f] |
| *Weisella viridescens* B-1951 | − | − | + | +++ | NT | NRRL |
| Yeast | | | | | | |
| *Saccharomyces carevisiae* | − | − | − | − | NT | NRRL |
| Gram negative | | | | | | |
| *Escherichia coli* DH5α | − | − | − | − | NT | Invitrogen |

[a]As measured by $OD_{600\ nm}$ decrease of whole cell suspensions (initial $OD_{600\ nm}$ = ~1)treated with lysin (10 μM) for 30 min. "+++" between 100% and 75% decrease, "++" between 74% and 50% decrease, "+" less than 49% decrease, "−" no decrease, with respect to no lysin control.
[b]ARS Culture Collection (also known as the NRRL Collection)
[c]Isolated from fermentors at a commercial dry-grind ethanol facility as described previously (Bischoff et al., 2009). *L. fermentum* 0315-1, 0315-25, and 0713-3 were planktonic isolates, and their MICs for virginiamycin are 16 mg/ml, ≤2 mg/ml, and ≤2 mg/ml, respectively. *L. fermentum* 0605-B44 was a biofilm isolate from coupon scrapings of a Center for Disease biofilm reactor inoculated with a mash sample from the fermentor.
[d]Channing Lab, Womens and Brigham Hospital, Boston, MA
[e]Dept. Biochemistry, Medical School, Univ. Alabama, Birmingham, AL
[f]Department of Veterinary Medicine, UMD, college Park MD
[g]NT (Not Tested)
[h]Results reported previously from this lab (Donovan and Foster-Frey, 2008, supra)

Example 2

Expression and Purification of Lysins

All lysin proteins were over-expressed in *E. coli* and purified via nickel column chromatography as previously described (Becker et al. 2009. *Gene* 443:32-41). Purified pET21a harboring the lysin genes of interest, were transformed into *E. coli* BL21(DE3) (Invitrogen, Carlsbad, Calif.) by heat shock at 42° C. for 30 s. BL21(DE3) transformants were cultured at 37° C. in 1 L modified LB (mLB) medium (15 g/l tryptone, 8 g/l yeast extract, 5 g/l NaCl) supplemented with 150 μg/ml ampicillin. Mid log phase ($OD_{600\ nm}$ of 0.4-0.6) cultures were induced with 1 mM IPTG (isopropyl-beta-D-thiogalactopyranoside), followed by 10° C. overnight incubation. Induced cells were pelleted, resuspended in 10 mL of lysis buffer (50 mM NaH2PO4, 300 mM NaCl, 10 mM imidazole, 30% glycerol, pH 8.0), and sonicated on ice for 15 min (1 s pulses separated by 1 s rests). After centrifugation (9000×g for 30 min), proteins were purified from the cleared supernatant by immobilized metal ion affinity chromatography, using nickel-NTA Superflow resin (QIAGEN, Valencia, Calif.). Resin was washed with 40 column volumes (CV) of lysis buffer, and 15 CV of wash buffer (50 mM NaH2PO4, 300 mM NaCl, 20 mM imidazole, 30% glycerol, pH 8.0). His$_6$-tagged proteins were eluted with elution buffer (50 mM $NaH_2PO_4$, 300 mM NaCl, 250 mM imidazole, 30% glycerol, pH 8.0) to achieve >90% purity. Protein elutes were filter sterilized (0.22 μm), concentration measured spectrophotometrically using a NanoDrop ND-1000 (NanoDrop Technologies, Wilmington, Del.), and purities were determined via sodium dodecyl sulfate-polyacrylamide gel electrophoresis (SDS-PAGE).

Figure 2:
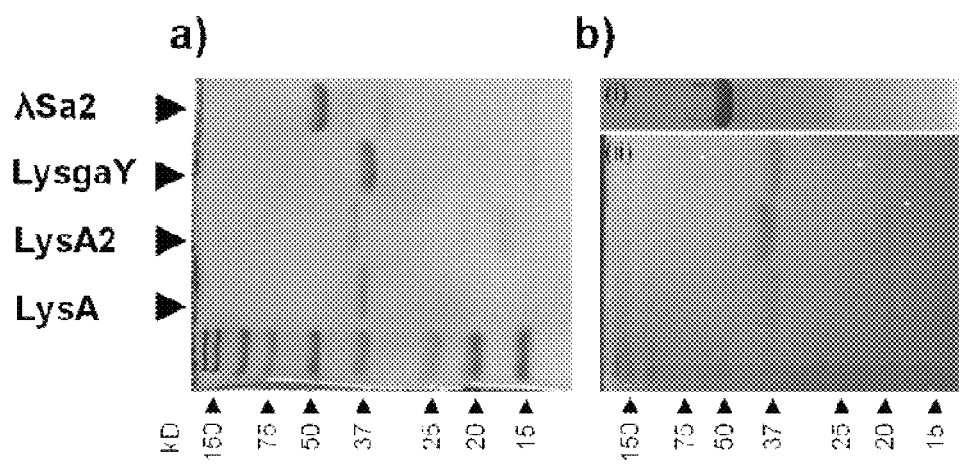
FIGS. 2a and 2b depict SDS-PAGE and exolytic activity analyses of immobilized metal affinity chromatography-purified recombinant lysins.

Induction and purification of putative lytic proteins, λSa2 endolysin, LysgaY, LysA2, and LysA occurred without complication. SDS-PAGE analysis of the nickel chromatography-purified proteins produced prominent bands for λSa2 endolysin, LysgaY, LysA2, and LysA that migrated to positions in the SDS PAGE consistent with their predicted molecular masses of 51.9 kD, 37.4 kD, 33.9 kD, and 36.4 kD, respectively (FIG. 2a).

We were unable to purify the remaining three of the seven cloned putative lytic proteins, ABJ8901 [GenBank:

ABJ8901], BAG8101 [GenBank: BAG8101] and Lyb5 from phiPBY5 (Wang et al. 2008. *J. Appl. Microbiol.* 105:1939-1944), due to complications during IPTG induction of *E. coli* BL21(DE3) transformed cells. After induction, the *E. coli* culture unexpectedly autolysed leading to culture failure (data not shown).

Example 3

Zymogram and Turbidity Reduction Assays

The purified proteins and Kaleidoscope protein standards (Bio-Rad) were analyzed using 15% SDS-PAGE, with or without 300 mL equivalent of mid log phase ($OD_{600\ nm}$ of 0.4-0.6) lactobacilli cells that were pelleted, and washed twice in buffer (50 mM NaH2PO4, 150 mM NaCl, pH 8.0) prior to addition to the pre-polymerized gel. Gels were electrophoresed at 150 volts (~1 h). SDS-PAGE gels were Coomassie stained and zymograms were washed in excess $H_2O$ for 1 h and incubated at 24° C. in 50 mM Tris-HCl, 1% Triton X114, pH 5.5, until visible translucent bands appeared and images taken (~18 h).

The turbidity assays were performed in a Molecular Devices Spectra Max 340 plate reader. Strains were grown to mid-log phase ($OD_{600\ nm}$=0.4-0.6) at 37° C., washed in buffer (20 mM phosphate, 150 mM NaCl, 30% glycerol: pH 8.0), pelleted, and frozen at ~80° C. Cells were thawed on ice and resuspended to $OD_{600\ nm}$=2.0 in buffer (20 mM phosphate, 150 mM NaCl: pH 5.5, unless otherwise stated). Lysins were standardized to 1 µM per well and the assay started by the addition of 100 µL of cell suspension, giving an initial $OD_{600\ nm}$=1. Immediately, absorbance ($OD_{600\ nm}$) readings were taken every 30 s for 30 min and specific activities were determined on a sliding scale as described by Becker et al. (2008, supra) as $OD_{600\ nm}$/min/µM. Control samples with cells alone (no enzyme) were included, and 'cells alone' specific activities were subtracted from experimental sample specific activities control for the effect of autolysis.

Zymogram analysis was performed with whole cells of *L. reuteri* 14171 or *L. amylovorus* 4540 co-polymerized within the polyacrylamide gel matrix (FIG. 2b). Single translucent or dark bands indicate lysis of the embedded cells were observed in each lane at approx. 52 kD, 38 kD, 35 kD, and 37 kD in agreement with the predicted MW of λSa2 endolysin, LysgaY, LysA2, and LyaA, as indicated by SDS-PAGE (FIG. 2a), respectively.

Purified lysin constructs were tested in turbidity reduction assays for their ability to lyse log phase cultures of several bacterial species (Table 2). The λSa2 endolysin construct had strong lytic activity towards 17 of 22 lactobacilli, staphylococci or streptococci, and weaker activity towards another three. The truncated λSa2-ECC construct was only tested on two *Lactobacillus* strains in this study, but had been shown previously to be lytic for numerous streptococci and staphylococci. LysA, LysA2 and LysgaY constructs had similar exolytic host ranges towards ~60% of the lactobacilli tested including all four *L. fermentum* isolates, and *L. gasseri*, *L. brevis* and *L. reuteri*. LysA was able to reduce cell populations >75% for 50% of the sensitive strains and >50% for the remaining strains tested. However, LysA2 and LysgaY were only able to decrease cellular turbidity by <50%. Interestingly, LysA and LysgaY had exolytic activity towards 100% of the streptococci and 80% of the staphylococci tested, whereas LysA2 did not show any exolytic activity towards the non lactic acid bacteria species tested. None of the lysin constructs tested had exolytic activity towards the Gram negative *E. coli* DH5α or the yeast strain of *S. cerevisiae*.

Figure 3:
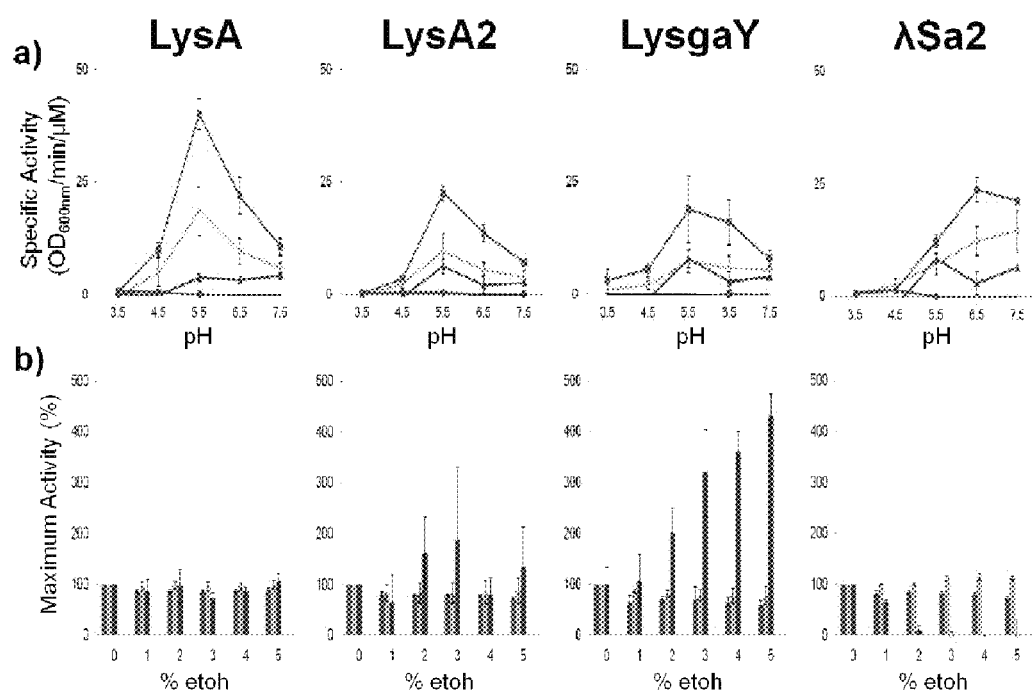
FIG. 3 is a turbidity reduction analysis of LysA, LysA2, LysgaY and λSa2 endolysin constructs against multiple lactobacilli under a range of pH and ethanol concentrations.

The functional properties for lysins LysA, LysA2, LysgaY and λSa2 endolysin were tested under a range of pH and ethanol concentrations with turbidity reduction analysis using live whole cells of *L. fermentum* strains 0605-B44 and 0315-1, and *L. brevis* strain 0605-48, as substrate. Optimal specific activity was achieved for LysA, LysA2, and LysgaY at pH 5.5, although these lysins demonstrated strong exolytic activity between pH 5.5 and pH 6.5 (FIG. 3a). For these three lysins, the presence of ethanol (≤5%) in the turbidity reduction assay did reduce the maximum activity achieved (FIG. 3b). However, LysgaY activity improved approximately 3 fold when *L. brevis* was used as substrate in the presence of 3% ethanol and nearly 5 fold at 5% ethanol. The streptococci phage λSa2 endolysin produced its optimal specific activity at a slightly higher pH of 6.5 and also was not affected by the presence of ethanol (≤5%) for both *L. fermentum* substrates. However, activity with *L. brevis* substrate in ≤1% ethanol completely abolished exolytic activity.

Example 4

Mock Fermentation and Sensitivity of Exolytic Activity to pH and Ethanol

Corn fiber, obtained from a commercial wet-mill ethanol facility, was hydrolyzed by dilute acid treatment as previously described (Bischoff et al. 2010. *Biotechnol. Lett.* 32:823-828). Briefly, sulfuric acid (1% w/v) was added to a suspension of corn fiber (10% w/v) and heated to 121° C. for 1 h, then neutralized to pH 5.5 with NaOH. The hydrolysate was cleared of particulate matter by centrifugation. Sterility was confirmed by plating aliquots of hydrolysate on MRS agar. The *S. cerevisiae* strain NRRL Y-2034 was grown overnight in YP broth supplemented with 4% (w/v) glucose at 32° C. with shaking at 200 rpm. Cells were harvested by centrifugation and resuspended in a volume of phosphate buffered saline (PBS; Fisher Scientific) pH7.4, necessary to obtain an $OD_{600\ nm}$ equivalent of 80. *L. fermentum* strain 0315-1 and *L. reuteri* strain B-14171 were grown to mid log phase ($OD_{600\ nm}$=0.4-0.6) (as described above), diluted appropriately in PBS to a density of $1 \times 10^5$ CFU/ml or $1 \times 10^8$ CFU/ml ($OD_{600\ nm}$=1.0 is ~$4.5 \times 10^8$ CFU/ml) and used as inoculums for mock fermentation analysis.

Mock fermentation cultures were prepared by combining 10 ml of corn fiber hydrosylate, 100 µl 12% $(NH_4)_2SO_4$, 150 µl cellulase (Celluclast; Novozymes, Bagsvaerd, Denmark), 150 µl Cellobiase (Novozyme 188; Novozymes), and 125 µl *S. cerevisiae* ($OD_{600\ nm}$ equivalent of 80), in a 50 ml conical tube. For each lysin treatment analyses, 800 µl of mock fermentation prep was spiked with 100 µl mid log phase lactic acid bacteria cells ($1 \times 10^5$ CFU/ml or $1 \times 10^8$ CFU/ml), and treated with 100 µl purified $His_6$-tagged lysin. 'No-lysin' controls were included. Mock fermentations were cultured at 30° C. with aliquots taken at 0 min, 30 min, and 60 min intervals. The aliquots were titered by plating on 1.5% MRS agar containing 100 µg/ml cyclohexamide (to inhibit growth of *S. cerevisiae*) and incubated anaerobically using the AnaeroPack System (Mitsubishi, Tokyo, Japan) at 37° C. for 24 h.

Figure 4:
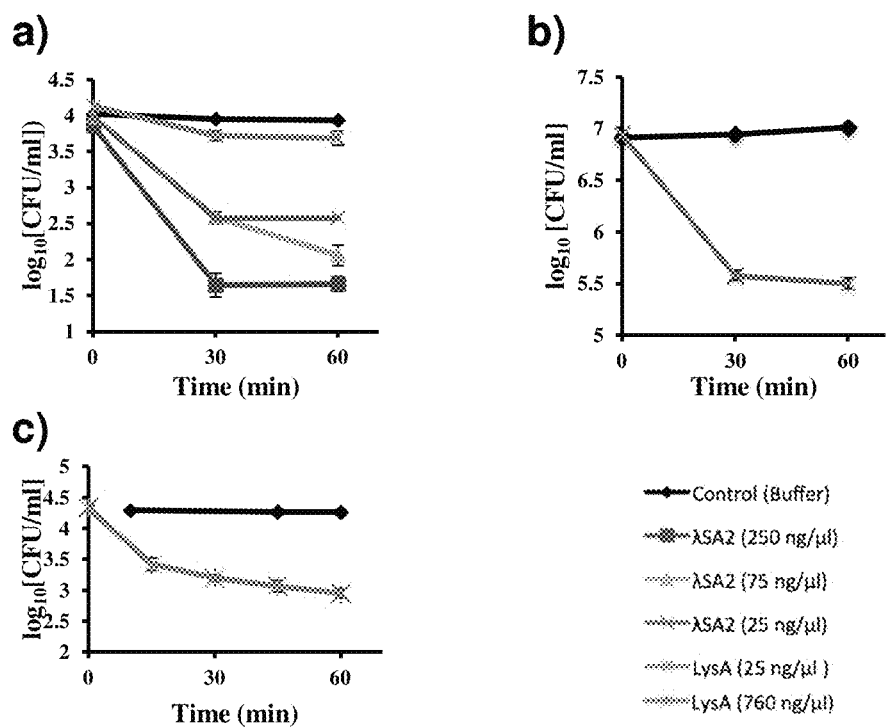
FIGS. 4a, 4b, and 4c depict λSA2 and LysA exolytic activity in mock fermentations of corn fiber hydrolysates inoculated with *L. fermentum* and *L. reuteri*.

Industrial fermentation substrates have high sugar concentrations, and, for hydrolysates of lignocellulosic biomass, may also contain lignin degradation products (e.g. phenolic acids, acetic acid, and furfural). To test whether this environment may inhibit our lysins, we tested the efficacy of the lysin λSA2 and LysA to reduce viable *L. fermentum* (BR0315-1) and *L. reuteri* (B-14171) in mock fermentations of corn fiber hydrolysates. λSA2 endolysin was tested at a final concentration of 250 ng/µl, 75 ng/µl, and 25 ng/µl in a fermentation experimentally inoculated with $1 \times 10^4$ CFU/ml *L. fermentum*. Bacterial loads in cultures treated with λSA2 endolysin decreased within 30 min, and by 60 min, reductions in bacterial concentration ranged from ~1.5 $\log_{10}$ (CFU/ml) at 25 ng/µl λSA2 endolysin to ~2.5 $\log_{10}$ (CFU/ml) at 250 ng/µl λSA2 endolysin (FIG. 4a). LysA had diminished exolytic activity compared to λSA2 endolysin, generating a reduction of only ~0.45 $\log_{10}$ (CFU/ml) in hydrolysates containing $1 \times 10^4$ CFU/ml (FIG. 4a). LysA was also tested against *L. reuteri* to demonstrate lysin abilities to kill other *Lactobacillus* species (FIG. 4c). In hydrolysates spiked with 4 $\log_{10}$ (CFU/ml) *L. reuteri*, LysA was able to reduce inoculum by ~1.39 $\log_{10}$ (CFU/ml) (FIG. 4c).

Since contaminating bacterial loads in commercial fermentation cultures may reach $10^6$ to $10^8$ CFU/ml (Skinner and Leathers, supra), the λSA2 endolysin (25 ng/µl) was tested against $10^7$ CFU/ml *L. fermentum* BR0315-1. After 60 min, λSA2 endolysin reduced bacterial load from 7.0 $\log_{10}$ (CFU/ml) to 5.5 $\log_{10}$ (CFU/ml) (FIG. 4b), a similar level of reduction shown in the mock fermentation contaminated with $1 \times 10^4$ CFU/ml *L. fermentum* (FIG. 4a). Untreated mock fermentations did not yield any reduction in contamination.

Thus, bacteriophage lytic enzymes are strong candidate antimicrobials to control lactic acid bacteria contamination in fuel ethanol fermentations. Four phage endolysins of Gram positive origin (LysA, LysA2, LysgaY and λSa2 endolysin) demonstrate lysis of lactic acid bacteria at pH and ethanol concentrations achieved during ethanolic fermentations. Two of these enzymes (λSA2 endolysin and LysA) reduce lactic acid bacteria by at least one log in mock fermentations. These qualities make these enzymes candidate antimicrobials for testing as either additives or engineered to be expressed by the fermentative yeast in biofuel ethanolic fermentations of corn or other feedstocks such as, wheat, triticale, barley, cassava, rye, graded starch stream rendered from feedstock, sugar cane, sugar beet, molasses, rice straw, potato waste, wood waste, switch grass, pine, municipal waste, food waste, alcoholic and non-alcoholic beverage industry waste and mixtures thereof.

Example 5

Expression of Lysins in Yeast (*Saccharomyces cerevisiae*)

The *Streptococcus* bacteriophage endolysin λSa2 gene in pET21A was amplified by polymerase chain reaction (PCR) in a 50 µl reaction volume using Easy-A High-Fidelity PCR Cloning Enzyme (Stratagene, 600400, La Jolla, Calif.) under the following conditions: one cycle at 95° C. for 2 min; 30 cycles of 95° C. for 40 s, 58° C. for 30 s, and 72° C. for 1.5 min; and finally one cycle at 72° C. for 7 min. The following primers were used for PCR: λSa2F: ATGGAAATCAA-CACTGAAATAGC (SEQ ID NO: 11); λSa2R: AACTG-GCTTTTAGTCAGTTC (SEQ ID NO: 12). The generated amplicon was cloned into the yeast expression vector pYes2.1 (Invitrogen, Carlsbad, Calif.) and transformed into *Saccharomyces cerevisiae* strain INVSc1 following the manufacturer's small-scale yeast transformation protocol.

The gene for the *Lactobacillus fermentum* Br11 endolysin LysA with a *Saccharomyces cerevisiae* codon bias was commercially synthesized and cloned into pUC57 vector by GenScript (Piscataway, N.J.). The gene was amplified by PCR in a 50 µl reaction volume using Easy-A High-Fidelity PCR Cloning Enzyme (Stratagene, 600400, La Jolla, Calif.) under the following conditions: one cycle at 95° C. for 2 min; 30 cycles of 95° C. for 40 s, 58° C. for 30 s, and 72° C. for 1.5 min; and finally one cycle at 72° C. for 7 min. The following primers were used for PCR: LysA_opt_F: ATGTTAAA AATGGTAGATGTATTCTCTGGTTCC (SEQ ID NO: 13); LysA_opt_nostop_R: TTCAAATTTACCGAATGGTTG-GTTAGTTTTAGCATCTCTA (SEQ ID NO: 14). The generated amplicon was cloned into the yeast expression vector pYes2.1 (Invitrogen, Carlsbad, Calif.) and transformed into *Saccharomyces cerevisiae* strain INVSc1 following the manufacturer's small-scale yeast transformation protocol.

Yeast Peptone Dextrose Medium (YPD) [1% yeast extract, 2% peptone, and 2% dextrose (D-glucose)] was used to grow untransformed *S. cerevisiae* strain INVSc1 and transformed yeast was grown on synthetic drop-out medium containing yeast nitrogen base without amino acids (0.67%), 2% glucose, and supplemented with amino acids. Drop-out medium without uracil contained all standard amino acids (76 mg/L final) plus leucine (380 mg/L final) and lacking uracil (Sigma, Y1501, Sigma, St. Louis, Mo.). Induction medium was similar to synthetic drop-out medium except that glucose was supplemented with filter-sterilized galactose (final concentration of 2%). Glucose and galactose were filter-sterilized using the Nalgene Rapid-Flow 0.20 µm Polyethersulfone (PES) filter unit (595-4520, Pittsburgh, Pa.).

Figure 5A:
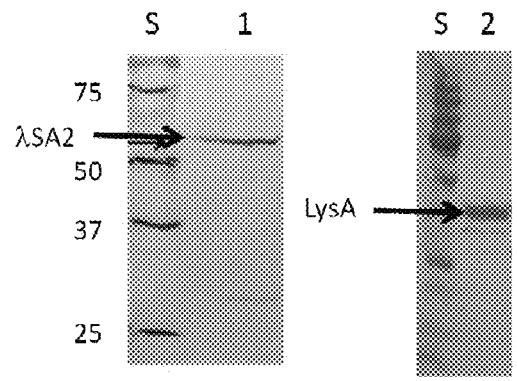
FIG. 5a is Western blot analysis of whole cells expressing either λSA2 endolysin (lane 1) or LysA (lane 2) constructs. Cells were boiled in SDS-sample loading buffer and applied to a SDS-PAGE gel, transferred to nitrocellulose membrane, and analyzed by Western blot using an anti-poly-histidine antibody as primary antibody. A band of approximately 54 kDa in lane 1 and 38 kDa in lane 2 represent the expressed λSA2 endolysin and LysA constructs, respectively.

Liquid drop-out medium containing the appropriate selective amino acids, was inoculated with transformed yeast cells from a plate, and grown at 30° C. overnight. The overnight culture was used to inoculate a culture containing induction medium. Induced cultures were grown at 30° C. with shaking (180 rpm) for up to 4 days. The lysins cloned in pYes2.1 and expressed in *S. cerevisiae* possess a carboxy-terminal polyhistidine tag that allows for detection of recombinant protein by Western blot using anti-His (C-terminal) antibodies (Life Technologies Corporation, Grand Island, N.Y.). FIG. 5a shows the Western blot analysis of transformed yeast cells expressing either λSa2 (lane 1) or LysA (lane 2). Signals of approximately 54 kDa (lane 1) and 38 kDa (lane 2) are visible, corresponding to the expected masses of λSa2 and LysA, respectively.

Figure 5B:
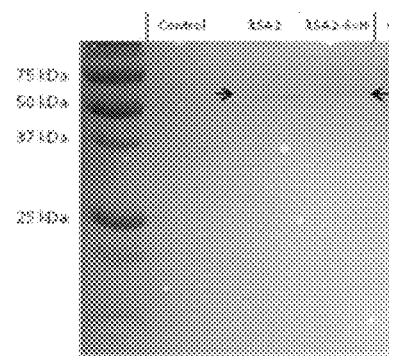
FIG. 5b is a zymogram analysis of *S. cerevisiae* expressing λSA2 endolysin construct. Two constructs of the λSA2 gene, with and without a C-terminal polyhistidine tag (λSA2 and λSA2-His$_6$-tag, respectively), were transformed and expressed in *S. cerevisiae* INVSc1. Whole cells were harvested and boiled in SDS-sample buffer solution, and applied to SDS-PAGE gel containing *Streptococcus agalactiae* co-polymerized within the polyacrylamide gel. Lysin exolytic activity resulted in visible clearing (dark bands indicated by arrows) of the cell substrate at the point of protein localization, which corresponds with predicted molecular weight.

Yeast-expressed λSa2 was tested for activity by zymogram analysis. Zymogram analysis was performed with whole cells of *Streptococcus agalactiae* co-polymerized within the polyacrylamide gel matrix. Two constructs of the λSA2 gene, with and without a C-terminal polyhistidine tag (λSA2 and λSA2-His$_6$-tag, respectively), were transformed and expressed in *S. cerevisiae* INVSc1. Whole cells were harvested and boiled in SDS-sample buffer solution, and applied to the gel. Gels were washed in excess $H_2O$ for 1 h and incubated at 24° C. in 50 mM Tris-HCl, 1% Triton X100, pH 5.5, until visible translucent bands appeared. Single translucent or dark bands at the predicted molecular mass for λSa2 were observed in FIG. 5b (dark bands indicated by arrows), indicating lysis of the embedded cells. Thus, the λSa2 gene expressed in *S. cerevisiae* produces a functional lysin.

Yeast-expressed LysA was applied to an ethanol fermentation that was experimentally infected with *Lactobacillus fermentum*. Cells from 1 liter cultures of either *S. cerevisiae* INVSc1 or *S. cerevisiae* INVSc1 expressing LysA were harvested by centrifugation, and re-suspended in Y-PER solution (Thermo Scientific, Rockford, Ill.) to lyse the cells. The lysates were cleared of insoluble material by centrifugation. Erlenmeyer flasks (25 ml capacity) were filled with 18 ml YPD10 (10 g/l yeast extract, 20 g/l peptone, 100 g/l glucose) plus 1.25 ml of one of the following: water (infected); untransformed *S. cerevisiae* INVSc1 lysate (INVSc1), or *S. cerevisiae* expressing LysA lysate (LysA). Each flask was inoculated with 0.25 ml of *S. cerevisiae* Y2034 at a density of $OD_{600\ nm}$=8.0, and challenged with 0.25 ml of *L. fermentum* BR0315-1 at a density of $7\times10^6$ CFU/ml. Control fermentations (Control) included YPD10 media inoculated with *S. cerevisiae* Y2034 but not challenged with *L. fermentum* nor treated with any yeast lysate. Flasks were incubated at 32° C. and slowly agitated by shaking at 100 rpm. Samples (1 ml) were periodically assayed for ethanol concentration, and *L. fermentum* enumerated by plate counting on MRS agar.

Figure 5C:
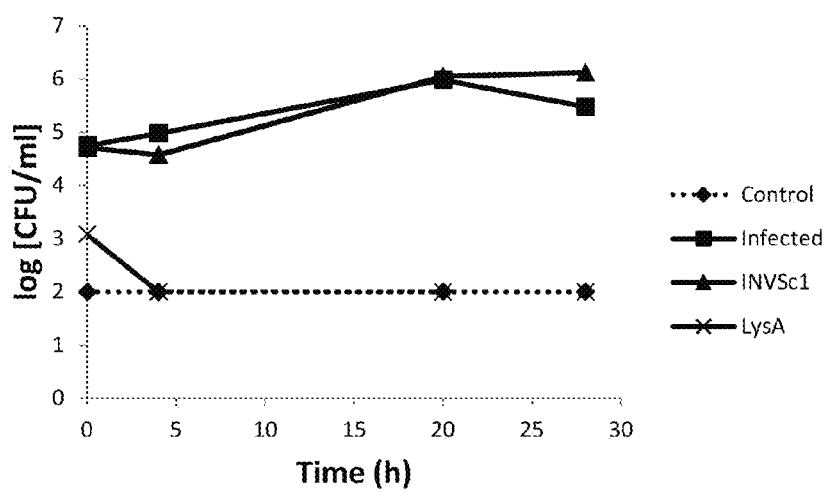
FIG. 5c depicts application of yeast-expressed LysA to fermentation of 10% (w/v) glucose in YP media. Fermentation cultures were experimentally infected with *Lactobacillus fermentum* and treated with either lysates of *S. cerevisiae* INVSc1 or of *S. cerevisiae* INVSc1 expressing LysA. *Lactobacillus* densities were enumerated by plate counting and compared to uninfected cultures (Control) and infected but untreated cultures (Infected). Treatment with LysA reduced *L. fermentum* CFU/ml to uninfected control levels (~$10^2$ CFU/ml) within 4 hours.

Treatment with lysates from *S. cerevisiae* expressing LysA reduced the *L. fermentum* population ~2 log [CFU/ml] within minutes of inoculation, and the bacterial population was below the limit of detection (2 log [CFU/ml]) within 4 h (FIG. 5c). Bacterial populations in cultures treated with the untransformed *S. cerevisiae* INVSc1 lysate were similar to those of the infected control, indicating that the observed reduction of *L. fermentum* was due to the presence of LysA in the lysate.

Final ethanol yield in the control fermentation was 48.4±0.2 g/l while that in the LysA treated fermentation was 48.1±0.1 g/l, suggesting that LysA had minimal effect on ethanol production by the *S. cerevisiae* Y2034 microbial catalyst.

All publications and patents mentioned in this specification are herein incorporated by reference to the same extent as if each individual publication or patent was specifically and individually indicated to be incorporated by reference.

The foregoing description and certain representative embodiments and details of the invention have been presented for purposes of illustration and description of the invention. It is not intended to be exhaustive or to limit the invention to the precise forms disclosed. It will be apparent to practitioners skilled in this art that modifications and variations may be made therein without departing from the scope of the invention.

---

We claim:

1. A method of controlling bacterial contamination in ethanol fermentation comprising: introducing a fermentation mixture comprising yeast *S. cerevisiae* into a vessel used during ethanol production; introducing a recombinant bacteriophage lytic endolysin as an active agent to the vessel used during ethanol production, and fermenting the fermentation mixture by said yeast to produce ethanol; wherein the recombinant endolysin is an antimicrobial agent having exolytic activity for at least one targeted Gram positive lactic acid bacterial species in an amount effective to at least reduce the levels of growth of and colonization by at least one targeted lactic acid bacterial species present in the vessel during ethanol production without inhibiting the growth of said yeast in the vessel thereby resulting in increased ethanol production from the fermentation mixture.

2. A method of controlling lactic acid bacterial contamination in ethanol fermentation comprising: introducing a fermentation mixture comprising yeast *S. cerevisiae* into a vessel used during ethanol production; introducing a recombinant yeast host cell comprising genes encoding a recombinant bacteriophage lytic endolysin as an active agent to the vessel used during ethanol production, and fermenting the fermentation mixture by said yeast to produce ethanol; wherein the recombinant endolysin is an antimicrobial agent having exolytic activity for at least one targeted Gram positive lactic acid bacterial species in an amount effective to at least reduce the levels of growth of and colonization by at least one targeted lactic acid bacterial species present in the vessel during ethanol production without inhibiting the growth of said fermenting yeast or recombinant yeast host cells in the vessel thereby resulting in increased ethanol production from the fermentation mixture.

3. A method of controlling lactic acid bacterial contamination in ethanol fermentation comprising: introducing a fermentation mixture comprising yeast *S. cerevisiae* into a vessel used during ethanol production; introducing a recombinant yeast extract from a host cell comprising genes encoding a recombinant bacteriophage lytic endolysin as an active agent to the vessel used during ethanol production, and fermenting the fermentation mixture by said yeast to produce ethanol; wherein the recombinant endolysin is an antimicrobial agent having exolytic activity for at least one targeted Gram positive lactic acid bacterial species in an amount effective to at least reduce the levels of growth of and colonization by at least one targeted lactic acid bacterial species present in the vessel during ethanol production without inhibiting the growth of said fermenting yeast or recombinant yeast host cells in the vessel thereby resulting in increased ethanol production from the fermentation mixture.

4. The method of claim 1, 2 or 3, wherein said targeted Gram positive bacterial species is *Lactobacillus* sp., *Staphyloccocus* sp., *Streptococcus* sp. *Weisella* sp., *Leuconostoc* sp., *Propionicbacterium* sp. or *Clostridium* sp.

5. The method of claim 1, 2 or 3, wherein said recombinant bacteriophage lytic endolysin is LysA, LysA2, LysgaY, λSa2 or truncated λSa2 endolysin.

6. The method of claim 1, 2 or 3, wherein the ethanol produced is fuel ethanol.

7. The method of claim 1, wherein the vessel is a fermentation tank and the recombinant endolysin is introduced therein.

8. The method of claim 2, wherein the vessel is a fermentation tank and the recombinant yeast host cell comprising genes encoding a recombinant phage lytic endolysin as an active agent is introduced therein.

9. The method of claim 3, wherein the vessel is a fermentation tank and the recombinant yeast extract is from a host cell comprising genes encoding a recombinant phage lytic endolysin as an active agent is introduced therein.

10. The method of claim 7, wherein the recombinant endolysin is introduced into the vessel early during ethanol production, when the ethanol concentration is low, or later during ethanol production, when the ethanol concentration has become higher or at several times during ethanol production.

11. The method of claim 8, wherein the recombinant yeast host cell comprising genes encoding a recombinant phage lytic endolysin as an active agent is introduced into the vessel early during ethanol production, when the ethanol concentration is low, or later during ethanol production, when the ethanol concentration has become higher or at several times during ethanol production.

12. The method of claim 9, wherein the recombinant yeast extract is from a host cell comprising genes encoding a recombinant phage lytic endolysin as an active agent is introduced into the vessel early during ethanol production, when the ethanol concentration is low, or later during ethanol production, when the ethanol concentration has become higher or at several times during ethanol production.

13. The method of claim 1, wherein the vessel is a yeast propagation tank and the recombinant phage lytic endolysin is introduced therein.

14. The method of claim 2, wherein the vessel is a yeast propagation tank and the recombinant yeast host cell comprising genes encoding a recombinant phage lytic endolysin as an active agent is introduced therein.

15. The method of claim 3, wherein the vessel is a yeast propagation tank and the recombinant yeast extract is from a host cell comprising genes encoding a recombinant phage lytic endolysin as an active agent is introduced therein.

16. The method of claim 1, 2, or 3, wherein the fermentation mixture is derived from a feedstock consisting essentially of: corn, wheat, triticale, barley, cassava, rye, graded starch stream rendered from said feedstocks, sugar cane, sugar beet, molasses, rice straw, potato waste, wood waste, switch grass, pine, municipal waste, food waste, alcoholic and non-alcoholic beverage industry waste.

\* \* \* \* \*

SEQUENCE LISTING

```
<160> NUMBER OF SEQ ID NOS: 14

<210> SEQ ID NO 1
<211> LENGTH: 942
<212> TYPE: DNA
<213> ORGANISM: Bacteriophage P2

<400> SEQUENCE: 1
catatgttaa aaatggttga tgtgttttct ggtagtcctc gtagttttgc aacattgcca      60
gaaaccgata ttacaatggt taaagctact caagggatag ggtatgttaa tccagcatgt     120
aatattgatt atgctaatgc aaaagcagca ggaaagttac taggtttata ccactattgt     180
gctggtggta atccaattgc agaagctgat tacttcatta ataatattaa aaactatgtg     240
ggtgaagcag tcctagcggt tgactgggaa ggatatcaaa actctagttg gggtaattac     300
aattatgtac gtcaatttgt taaccgtgtt catgagttaa caggcgtgtg gtgcatggtt     360
tatgtatctc agtctgaaat tcgacaagtt gcaaactgta taaatgattg tccactttgg     420
gttgcttact acaagtattc gcaacctctt aattgggatt atcaaggtgc tgggtttaac     480
attgcccctt gggaagtatt taccattcat caattcactg gttcagatat ggatcggaat     540
atggttaata caactaaaga aggctggtta agatggcta actctaataa caatatttct     600
attccagaac cttctcctat tcaaccggta gaagaacgca aggatgagaa agaagtatca     660
tttgttgatg atctaggcga tacttggttt aaggaagatg gcaagttcac cctagatgta     720
ggggttaatt tacgctatgg tgcccgaaca acatctaata ttattgctac tttaccagca     780
ggatctacta ttaagtatga tgcctttagt cgtcacgctg gctatgtttg gattcgtcaa     840
ccacgagaaa acggttatgg ttacatggct gttcgtgatg ctaagactaa ccaacctttt     900
ggaaaatttg aataactcga gcaccaccac caccaccact ga                        942

<210> SEQ ID NO 2
<211> LENGTH: 311
<212> TYPE: PRT
<213> ORGANISM: Bacteriophage P2

<400> SEQUENCE: 2

Met Leu Lys Met Val Asp Val Phe Ser Gly Ser Pro Arg Ser Phe Ala
1               5                   10                  15

Thr Leu Pro Glu Thr Asp Ile Thr Met Val Lys Ala Thr Gln Gly Ile
            20                  25                  30

Gly Tyr Val Asn Pro Ala Cys Asn Ile Asp Tyr Ala Asn Ala Lys Ala
        35                  40                  45
```

```
Ala Gly Lys Leu Leu Gly Leu Tyr His Tyr Cys Ala Gly Gly Asn Pro
 50                  55                  60

Ile Ala Glu Ala Asp Tyr Phe Ile Asn Ile Lys Asn Tyr Val Gly
 65              70                  75                  80

Glu Ala Val Leu Ala Val Asp Trp Gly Tyr Gln Asn Ser Ser Trp
                 85                  90                  95

Gly Asn Tyr Asn Tyr Val Arg Gln Phe Val Asn Arg Val His Glu Leu
             100                 105                 110

Thr Gly Val Trp Cys Met Val Tyr Val Ser Gln Ser Glu Ile Arg Gln
             115                 120                 125

Val Ala Asn Cys Ile Asn Asp Cys Pro Leu Trp Val Ala Tyr Tyr Lys
130                 135                 140

Tyr Ser Gln Pro Leu Asn Trp Asp Tyr Gln Gly Ala Gly Phe Asn Ile
145                 150                 155                 160

Ala Pro Trp Glu Val Phe Thr Ile His Gln Phe Thr Gly Ser Asp Met
                165                 170                 175

Asp Arg Asn Met Val Asn Thr Thr Lys Glu Gly Trp Leu Lys Met Ala
            180                 185                 190

Asn Ser Asn Asn Asn Ile Ser Ile Pro Glu Pro Ser Pro Ile Gln Pro
            195                 200                 205

Val Glu Glu Arg Lys Asp Glu Lys Glu Val Ser Phe Val Asp Asp Leu
210                 215                 220

Gly Asp Thr Trp Phe Lys Glu Asp Gly Lys Phe Thr Leu Asp Val Gly
225                 230                 235                 240

Val Asn Leu Arg Tyr Gly Ala Arg Thr Thr Ser Asn Ile Ile Ala Thr
                245                 250                 255

Leu Pro Ala Gly Ser Thr Ile Lys Tyr Asp Ala Phe Ser Arg His Ala
            260                 265                 270

Gly Tyr Val Trp Ile Arg Gln Pro Arg Glu Asn Gly Tyr Gly Tyr Met
            275                 280                 285

Ala Val Arg Asp Ala Lys Thr Asn Gln Pro Phe Gly Lys Phe Glu Leu
290                 295                 300

Glu His His His His His
305                 310

<210> SEQ ID NO 3
<211> LENGTH: 1080
<212> TYPE: DNA
<213> ORGANISM: Lactobacillus casei bacteriophage A2

<400> SEQUENCE: 3
catatgtcct acacgattaa taaagaattt gctctgggtg ctaacgaagg ttcatctcaa      60
gtggctaacc gcctgtatat catcctgcat gatgttggtg ccgaaagcgg tgcacgtgct     120
aatgccgcat acttcaagaa caacatctct gcggaaatcg cctacacggc attcgtggtt     180
ggtgatggcg tcaggtttta tcaagttggt gaaccgggtt atgttcagtg gggtgcgggt     240
accgttgcca acgccaattc accggtccaa attgaactgg tcatacgtc ggatccggaa      300 acctttaaaa aggactatgc ggtctacatt gaactggccc gtgatatggc agctcgctat     360
ggcatcccga cgtcactgga tgctggcggt gccggtaccc cgggtattaa atcgcacctg     420
tgggtgacgc agcatatctg gggtgatcac accgacccgt atggttacct ggcgcgttgg     480
ggcatcacga agaaaaaact ggccgcggat ctggccaatg gtaccaccac cgttgacgcc     540
agcacctctg caccggctac ccagagtacc cgtccgcaag caacggtctc cggtaacgtg     600
```

-continued

```
aatgctacct atggcctgca tctgctgggc ggtagctggc tggatgaagt gaccaacttt    660
ggctctggtg acaatggctt cgcgggtatg ccgaatcatc agcacgatct gctgtatatt    720
cgtgttgacc atggcagtgt caaataccgc gtgcacaccg ttcaatccgg ttggctggat    780
tgggtgacga agggcgatcg caacgacacc gttaatggct gcgccggtat tgcaggcgaa    840
gctatcgatg gtgtgcagat tatcttcctg accccggcag gcgaaccgta tcagcaagct    900
tattaccgtt cacagaccac ccaacgtgcg ggttggctgg gtgtcgtgtg tgatgacggt    960
acctccctgc gcagtatac gggcacctac gcaggcctgt ttggtgaacc gctggaccgt   1020
ctgcaaatcg gcatctcaag tatcaacccg tttctcgagc accaccacca ccaccactga  1080
```

<210> SEQ ID NO 4
<211> LENGTH: 358
<212> TYPE: PRT
<213> ORGANISM: Lactobacillus casei bacteriophage A2

<400> SEQUENCE: 4

```
Met Ser Tyr Thr Ile Asn Lys Glu Phe Ala Leu Gly Ala Asn Glu Gly
1               5                   10                  15

Ser Ser Gln Val Ala Asn Arg Leu Tyr Ile Ile Leu His Asp Val Gly
            20                  25                  30

Ala Glu Ser Gly Ala Arg Ala Asn Ala Ala Tyr Phe Lys Asn Asn Ile
        35                  40                  45

Ser Ala Glu Ile Ala Tyr Thr Ala Phe Val Val Gly Asp Gly Gly Gln
    50                  55                  60

Val Tyr Gln Val Gly Glu Pro Gly Tyr Val Gln Trp Gly Ala Gly Thr
65                  70                  75                  80

Val Ala Asn Ala Asn Ser Pro Val Gln Ile Glu Leu Gly His Thr Ser
                85                  90                  95

Asp Pro Glu Thr Phe Lys Lys Asp Tyr Ala Val Tyr Ile Glu Leu Ala
            100                 105                 110

Arg Asp Met Ala Ala Arg Tyr Gly Ile Pro Thr Ser Leu Asp Ala Gly
        115                 120                 125

Gly Ala Gly Thr Pro Gly Ile Lys Ser His Leu Trp Val Thr Gln His
    130                 135                 140

Ile Trp Gly Asp His Thr Asp Pro Tyr Gly Tyr Leu Ala Arg Trp Gly
145                 150                 155                 160

Ile Thr Lys Glu Lys Leu Ala Ala Asp Leu Ala Asn Gly Thr Thr Thr
                165                 170                 175

Val Asp Ala Ser Thr Ser Ala Pro Ala Thr Gln Ser Thr Arg Pro Gln
            180                 185                 190

Ala Thr Val Ser Gly Asn Val Asn Ala Thr Tyr Gly Leu His Leu Leu
        195                 200                 205

Gly Gly Ser Trp Leu Asp Glu Val Thr Asn Phe Gly Ser Gly Asp Asn
    210                 215                 220

Gly Phe Ala Gly Met Pro Asn His Gln His Asp Leu Leu Tyr Ile Arg
225                 230                 235                 240

Val Asp His Gly Ser Val Lys Tyr Arg Val His Thr Val Gln Ser Gly
                245                 250                 255

Trp Leu Asp Trp Val Thr Lys Gly Asp Arg Asn Asp Thr Val Asn Gly
            260                 265                 270

Cys Ala Gly Ile Ala Gly Glu Ala Ile Asp Gly Val Gln Ile Ile Phe
        275                 280                 285
```

```
Leu Thr Pro Ala Gly Glu Pro Tyr Gln Gln Ala Tyr Tyr Arg Ser Gln
    290                 295                 300

Thr Thr Gln Arg Ala Gly Trp Leu Gly Val Val Cys Asp Asp Gly Thr
305                 310                 315                 320

Ser Leu Pro Gln Tyr Thr Gly Thr Tyr Ala Gly Leu Phe Gly Glu Pro
                325                 330                 335

Leu Asp Arg Leu Gln Ile Gly Ile Ser Ser Ile Asn Pro Phe Leu Glu
                340                 345                 350

His His His His His His
        355
```

<210> SEQ ID NO 5
<211> LENGTH: 963
<212> TYPE: DNA
<213> ORGANISM: Lactobacillus gasseri

<400> SEQUENCE: 5

```
catatggttg aagtagctaa agaagttac ggtgtagatg tatcaagtca taacaacggc      60
aattattccg gatcgaaatt tgccgttgtt aaagtgtcag agggcttaga ttatcgtaat    120
cctaaagcac aatctcaagt atctactgca agagctaata gtatgttgcc aatggcttat    180
cactatgcga ggtttagtgg caatagtaac gtagcaattc aagaaggtaa ctatgcagtt    240
acttctgcaa aagctgttgg tcttgaggca ggtacttact agcttgtga ctatgaacaa     300
ggaagtggaa acgaaactag aggagatcgt gaaactaata cgactgctat cttatctttc    360
ttagatacta ttgtgggtgc tggttataag cctttactat actcaggcgc ttatcttatg    420
agagacaaaa ttaatacttc tagaattta gccaagtatc ctaattgttt gtgggtagca     480
gcatatccat caggtaatgg tactgcggta agtgaaccaa actttggcta ctttccatca    540
atgaacggag tagcaatttg gcaatttacc gataactggc gtgggttaaa tgttgacgga    600
aacatcagct tgattgatct aaaaaatgat agcaaaccag tagctcagcc atctgttgca    660
caatcagcat cagaaaaaac atggactgat gtacaaggta tgacttggca tgaagaacat    720
ggtactttca tcactggtgg agcgattaat cttcgctggg cgctaatac gcaaagcaca     780
ctgattacca ccttaccagc aggttcagaa gttaaataca atgcttgggc tagagatagt    840
gctgggcgtg tatggttaca gcaaccgaga gaaaatggta agaatggcta tttagttggt    900
cgtgtcggca gtgagccgtg gggaactttc aaataactcg agcaccacca ccaccaccac    960
tga                                                                   963
```

<210> SEQ ID NO 6
<211> LENGTH: 318
<212> TYPE: PRT
<213> ORGANISM: Lactobacillus gasseri

<400> SEQUENCE: 6

```
Met Val Glu Val Ala Lys Arg Ser Tyr Gly Val Asp Val Ser Ser His
1               5                   10                  15

Asn Asn Gly Asn Tyr Ser Gly Ser Lys Phe Ala Val Val Lys Val Ser
            20                  25                  30

Glu Gly Leu Asp Tyr Arg Asn Pro Lys Ala Gln Ser Gln Val Ser Thr
        35                  40                  45

Ala Arg Ala Asn Ser Met Leu Pro Met Ala Tyr His Tyr Ala Arg Phe
    50                  55                  60

Ser Gly Asn Ser Asn Val Ala Ile Gln Glu Gly Asn Tyr Ala Val Thr
65                  70                  75                  80
```

```
Ser Ala Lys Ala Val Gly Leu Glu Ala Gly Thr Tyr Leu Ala Cys Asp
                85                  90                  95

Tyr Glu Gln Gly Ser Gly Asn Glu Thr Arg Gly Asp Arg Glu Thr Asn
            100                 105                 110

Thr Thr Ala Ile Leu Ser Phe Leu Asp Thr Ile Val Gly Ala Gly Tyr
        115                 120                 125

Lys Pro Leu Leu Tyr Ser Gly Ala Tyr Leu Met Arg Asp Lys Ile Asn
    130                 135                 140

Thr Ser Arg Ile Leu Ala Lys Tyr Pro Asn Cys Leu Trp Val Ala Ala
145                 150                 155                 160

Tyr Pro Ser Gly Asn Gly Thr Ala Val Ser Glu Pro Asn Phe Gly Tyr
                165                 170                 175

Phe Pro Ser Met Asn Gly Val Ala Ile Trp Gln Phe Thr Asp Asn Trp
            180                 185                 190

Arg Gly Leu Asn Val Asp Gly Asn Ile Ser Leu Ile Asp Leu Lys Asn
        195                 200                 205

Asp Ser Lys Pro Val Ala Gln Pro Ser Val Ala Gln Ser Ala Ser Glu
    210                 215                 220

Lys Thr Trp Thr Asp Val Gln Gly Met Thr Trp His Glu Glu His Gly
225                 230                 235                 240

Thr Phe Ile Thr Gly Gly Ala Ile Asn Leu Arg Trp Gly Ala Asn Thr
                245                 250                 255

Gln Ser Thr Leu Ile Thr Thr Leu Pro Ala Gly Ser Glu Val Lys Tyr
            260                 265                 270

Asn Ala Trp Ala Arg Asp Ser Ala Gly Arg Val Trp Leu Gln Gln Pro
        275                 280                 285

Arg Glu Asn Gly Lys Asn Gly Tyr Leu Val Gly Arg Val Gly Ser Glu
    290                 295                 300

Pro Trp Gly Thr Phe Lys Leu Glu His His His His His
305                 310                 315

<210> SEQ ID NO 7
<211> LENGTH: 1437
<212> TYPE: DNA
<213> ORGANISM: Lambda Sa2 phage

<400> SEQUENCE: 7
catatggaaa tcaacactga aatagccatt gcctggatgt ctgcacgtca aggcaaggtc      60
agctattcca tggactaccg tgacggccct aacagctatg actgttccag ctctgtctat     120
tatgctctca ggtcagctgg tgcaagctca gcaggttggg cggtcaacac tgagtacatg     180
cacgattggc tgattaaaaa cggttatgag cttattgctg aaaacgtgga ttggaatgct     240
gtccgtggtg atatagcaat ttggggcatg cgagggcact caagcggagc tggtggtcat     300
gtagtcatgt ttattgaccc tgaaaatatc attcactgta actgggcaaa taatggcatc     360
acagtgaaca actacaatca gacagcggct gctagtggct ggatgtattg ctacgtttac     420
cgtttgaaaa gcggagcttc tacccaagga aaaagccttg ataccttggt caaggaaacc     480
cttgctggta actacggtaa tggcgaagca cgcaaggcag tgcttggcaa tcaatatgag     540
gctgttatgt cagtcatcaa tggcaaaact acgactaatc aaaagactgt tgaccaactt     600
gttcaagagg taatcgctgg caaacatggc aacggtgaag ctcgtaaaaa gtcgcttggt     660
agtcaatatg atgcagttca gaaacgagtg acggaattgc tcaaaaaaca gccctctgag     720
ccgtttaagg ctcaagaggt aaacaagccc acggaaacca aacaagccaa acagagcta      780
```

```
actggacaag ccacagccac caagaagag  ggcgacctct ctttcaatgg gactatcttg   840
aaaaaagcgg tgctggacaa gattctgggc aactgtaaaa agcatgatat tcttccaagt   900
tatgcactga ctatcctaca ctatgaaggt ctttggggaa cttcagcagt tgggaaggca   960
gataataact ggggcggtat gacctggact ggtcaaggca accgtccaag cggtgtcact  1020
gtcacacaag gttccgcacg tccttcaaat gagggcggtc actatatgca ctatgcaagc  1080
gtggatgact ttctgacaga ctggttttat cttctaaggg ctggtggctc ttacaaggtg  1140
tctggtgcta aaaccttcag tgaggctatc aagggaatgt ttaaagttgg cggtgctgtc  1200
tatgattatg ctgcaagcgg ctttgatagc tatattgtcg gagcttcaag ccgcctcaag  1260
gctattgagg cagaaaatgg ttcactggac aagtttgata aagctaccga cattggtgac  1320
ggtagcaaag acaagattga cattactatt gaaggtattg aagttaccat caacggtatc  1380
acttatgaac tgactaaaaa gccagtttag ctcgagcacc accaccacca ccactga      1437
```

<210> SEQ ID NO 8
<211> LENGTH: 476
<212> TYPE: PRT
<213> ORGANISM: Lambda Sa2 phage

<400> SEQUENCE: 8

Met Glu Ile Asn Thr Glu Ile Ala Ile Ala Trp Met Ser Ala Arg Gln
1               5                   10                  15

Gly Lys Val Ser Tyr Ser Met Asp Tyr Arg Asp Gly Pro Asn Ser Tyr
            20                  25                  30

Asp Cys Ser Ser Ser Val Tyr Tyr Ala Leu Arg Ser Ala Gly Ala Ser
        35                  40                  45

Ser Ala Gly Trp Ala Val Asn Thr Glu Tyr Met His Asp Trp Leu Ile
    50                  55                  60

Lys Asn Gly Tyr Glu Leu Ile Ala Glu Asn Val Asp Trp Asn Ala Val
65                  70                  75                  80

Arg Gly Asp Ile Ala Ile Trp Gly Met Arg Gly His Ser Ser Gly Ala
                85                  90                  95

Gly Gly His Val Val Met Phe Ile Asp Pro Glu Asn Ile Ile His Cys
            100                 105                 110

Asn Trp Ala Asn Asn Gly Ile Thr Val Asn Asn Tyr Asn Gln Thr Ala
        115                 120                 125

Ala Ala Ser Gly Trp Met Tyr Cys Tyr Val Tyr Arg Leu Lys Ser Gly
    130                 135                 140

Ala Ser Thr Gln Gly Lys Ser Leu Asp Thr Leu Val Lys Glu Thr Leu
145                 150                 155                 160

Ala Gly Asn Tyr Gly Asn Gly Glu Ala Arg Lys Ala Val Leu Gly Asn
                165                 170                 175

Gln Tyr Glu Ala Val Met Ser Val Ile Asn Gly Lys Thr Thr Thr Asn
            180                 185                 190

Gln Lys Thr Val Asp Gln Leu Val Gln Glu Val Ile Ala Gly Lys His
        195                 200                 205

Gly Asn Gly Glu Ala Arg Lys Lys Ser Leu Gly Ser Gln Tyr Asp Ala
    210                 215                 220

Val Gln Lys Arg Val Thr Glu Leu Leu Lys Lys Gln Pro Ser Glu Pro
225                 230                 235                 240

Phe Lys Ala Gln Glu Val Asn Lys Pro Thr Glu Thr Lys Thr Ser Gln
                245                 250                 255

```
Thr Glu Leu Thr Gly Gln Ala Thr Thr Lys Glu Glu Gly Asp Leu
            260                 265                 270

Ser Phe Asn Gly Thr Ile Leu Lys Lys Ala Val Leu Asp Lys Ile Leu
        275                 280                 285

Gly Asn Cys Lys Lys His Asp Ile Leu Pro Ser Tyr Ala Leu Thr Ile
        290                 295                 300

Leu His Tyr Glu Gly Leu Trp Gly Thr Ser Ala Val Gly Lys Ala Asp
305                 310                 315                 320

Asn Asn Trp Gly Gly Met Thr Trp Thr Gly Gln Gly Asn Arg Pro Ser
                325                 330                 335

Gly Val Thr Val Thr Gln Gly Ser Ala Arg Pro Ser Asn Glu Gly Gly
            340                 345                 350

His Tyr Met His Tyr Ala Ser Val Asp Asp Phe Leu Thr Asp Trp Phe
        355                 360                 365

Tyr Leu Leu Arg Ala Gly Gly Ser Tyr Lys Val Ser Gly Ala Lys Thr
370                 375                 380

Phe Ser Glu Ala Ile Lys Gly Met Phe Lys Val Gly Gly Ala Val Tyr
385                 390                 395                 400

Asp Tyr Ala Ala Ser Gly Phe Asp Ser Tyr Ile Val Gly Ala Ser Ser
                405                 410                 415

Arg Leu Lys Ala Ile Glu Ala Glu Asn Gly Ser Leu Asp Lys Phe Asp
            420                 425                 430

Lys Ala Thr Asp Ile Gly Asp Gly Ser Lys Asp Lys Ile Asp Ile Thr
        435                 440                 445

Ile Glu Gly Ile Glu Val Thr Ile Asn Gly Ile Thr Tyr Glu Leu Thr
        450                 455                 460

Lys Lys Pro Val Leu Glu His His His His His His
465                 470                 475

<210> SEQ ID NO 9
<211> LENGTH: 747
<212> TYPE: DNA
<213> ORGANISM: Lambda Sa2 phage

<400> SEQUENCE: 9
atggaaatca acactgaaat agccattgcc tggatgtctg cacgtcaagg caaggtcagc      60
tattccatgg actaccgtga cggccctaac agctatgact gttccagctc tgtctattat     120
gctctcaggt cagctggtgc aagctcagca ggttgggcgg tcaacactga gtacatgcac     180
gattggctga ttaaaaacgg ttatgagctt attgctgaaa acgtggattg gaatgctgtc     240
cgtggtgata tagcaatttg gggcatgcga gggcactcaa gcggagctgg tggtcatgta     300
gtcatgttta ttgaccctga aaatatcatt cactgtaact gggcaaataa tggcatcaca     360
gtgaacaact acaatcagac agcggctgct agtggctgga tgtattgcta cgtttaccgt     420
ttgaaaagcg gagcttctac ccaaggaaaa agccttgata ccttggtcaa ggaaacccttt    480 gctggtaact acggtaatgg cgaagcacgc aaggcagtgc ttggcaatca atatgaggct     540
gttatgtcag tcatcaatgg caaaactacg actaatcaaa agactgttga ccaacttgtt     600
caagaggtaa tcgctggcaa acatggcaac ggtgaagctc gtaaaaagtc gcttggtagt     660
caatatgatg cagttcagaa acgagtgacg gaattgctca aaaacagcc ctctgagccg      720 ctcgagcacc accaccaca ccactga                                         747
```

<210> SEQ ID NO 10
<211> LENGTH: 248
<212> TYPE: PRT
<213> ORGANISM: Lambda Sa2 phage

<400> SEQUENCE: 10

Met Glu Ile Asn Thr Glu Ile Ala Ile Ala Trp Met Ser Ala Arg Gln
1               5                   10                  15

Gly Lys Val Ser Tyr Ser Met Asp Tyr Arg Asp Gly Pro Asn Ser Tyr
            20                  25                  30

Asp Cys Ser Ser Ser Val Tyr Tyr Ala Leu Arg Ser Ala Gly Ala Ser
        35                  40                  45

Ser Ala Gly Trp Ala Val Asn Thr Glu Tyr Met His Asp Trp Leu Ile
    50                  55                  60

Lys Asn Gly Tyr Glu Leu Ile Ala Glu Asn Val Asp Trp Asn Ala Val
65                  70                  75                  80

Arg Gly Asp Ile Ala Ile Trp Gly Met Arg Gly His Ser Ser Gly Ala
                85                  90                  95

Gly Gly His Val Val Met Phe Ile Asp Pro Glu Asn Ile Ile His Cys
            100                 105                 110

Asn Trp Ala Asn Asn Gly Ile Thr Val Asn Asn Tyr Asn Gln Thr Ala
        115                 120                 125

Ala Ala Ser Gly Trp Met Tyr Cys Tyr Val Tyr Arg Leu Lys Ser Gly
    130                 135                 140

Ala Ser Thr Gln Gly Lys Ser Leu Asp Thr Leu Val Lys Glu Thr Leu
145                 150                 155                 160

Ala Gly Asn Tyr Gly Asn Gly Glu Ala Arg Lys Ala Val Leu Gly Asn
                165                 170                 175

Gln Tyr Glu Ala Val Met Ser Val Ile Asn Gly Lys Thr Thr Thr Asn
            180                 185                 190

Gln Lys Thr Val Asp Gln Leu Val Gln Glu Val Ile Ala Gly Lys His
        195                 200                 205

Gly Asn Gly Glu Ala Arg Lys Lys Ser Leu Gly Ser Gln Tyr Asp Ala
    210                 215                 220

Val Gln Lys Arg Val Thr Glu Leu Leu Lys Lys Gln Pro Ser Glu Pro
225                 230                 235                 240

Leu Glu His His His His His His
                245

<210> SEQ ID NO 11
<211> LENGTH: 23
<212> TYPE: DNA
<213> ORGANISM: Artificial Sequence
<220> FEATURE:
<223> OTHER INFORMATION: Chemically Synthesized

<400> SEQUENCE: 11
atggaaatca acactgaaat agc                                           23

<210> SEQ ID NO 12
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 12
aactggcttt ttagtcagtt c                                             21

```
<210> SEQ ID NO 13
<211> LENGTH: 33
<212> TYPE: DNA
<213> ORGANISM: Artificial Sequence
<220> FEATURE:
<223> OTHER INFORMATION: Chemically Synthesized

<400> SEQUENCE: 13
atgttaaaaa tggtagatgt attctctggt tcc                                 33

<210> SEQ ID NO 14
<211> LENGTH: 40
<212> TYPE: DNA
<213> ORGANISM: Artificial Sequence
<220> FEATURE:
<223> OTHER INFORMATION: Chemically Synthesized

<400> SEQUENCE: 14
ttcaaattta ccgaatggtt ggttagtttt agcatctcta                          40
```